(12) United States Patent
Ivarie et al.

(10) Patent No.: US 6,730,822 B1
(45) Date of Patent: May 4, 2004

(54) VECTORS IN AVIAN TRANSGENESIS

(75) Inventors: Robert D. Ivarie, Watkinsville, GA (US); Alex J. Harvey, Athens, GA (US); Julie A. Morris, Watkinsville, GA (US); Guodong Liu, Mississauga (CA); Jeffrey C. Rapp, Athens, GA (US)

(73) Assignee: AviGenics, Inc., Athens, GA (US)

( * ) Notice: Subject to any disclaimer, the term of this patent is extended or adjusted under 35 U.S.C. 154(b) by 0 days.

(21) Appl. No.: 09/173,864

(22) Filed: Oct. 16, 1998

Related U.S. Application Data

(60) Provisional application No. 60/062,172, filed on Oct. 16, 1997.

(51) Int. Cl.$^7$ ................. A01K 67/027; C12P 21/00; C12N 15/00; C12N 5/00; C12N 15/63

(52) U.S. Cl. ................. 800/19; 800/4; 800/8; 800/21; 800/23; 435/320.1; 435/325; 435/455

(58) Field of Search ................. 800/4, 8, 19, 21, 800/23, 25, 3; 435/320.1, 325, 455, 349

(56) References Cited

U.S. PATENT DOCUMENTS

| | | | |
|---|---|---|---|
| 4,959,317 A | 9/1990 | Sauer | 435/172.3 |
| 4,997,763 A | 3/1991 | Hughes et al. | 435/172.3 |
| 5,162,215 A | 11/1992 | Bosselman et al. | 435/172.3 |
| 5,304,489 A | 4/1994 | Rosen | 435/320.1 |
| 5,378,618 A | 1/1995 | Sternberg et al. | 435/172.3 |
| 5,464,764 A | 11/1995 | Capecchi et al. | 435/172.3 |
| 5,487,992 A | 1/1996 | Capecchi et al. | 435/172.3 |
| 5,677,177 A | 10/1997 | Wahl et al. | 435/325 |
| 5,741,957 A | 4/1998 | Deboer et al. | 800/2 |
| 5,784,992 A | * 7/1998 | Petitte et al. | 119/6.8 |

FOREIGN PATENT DOCUMENTS

| | | | |
|---|---|---|---|
| EP | 0 424 027 A1 | 4/1991 | |
| EP | 0 424 044 A1 | 4/1991 | |
| WO | WO 90/11355 | 10/1990 | |
| WO | WO 94/20608 | 9/1994 | |
| WO | WO 97/47739 | * 12/1997 | C12N/15/00 |
| WO | WO 98/01027 | 1/1998 | |

OTHER PUBLICATIONS

Sang TIBTECH 12:415–420, 1994.*
Simkiss, Transgenic birds, animals with novel genes, Mclean ed, Cambridge Univ.Press NY pp. 106–135 1994.*
Myllya et al, Biochem. J. 196:683–692, 1991.*
Myllya et al, Biochem J. 196:683–692, 1981.*
Thoraval et al Trans. Res. 4:369–376, 1995.*
Kotani et al Hum. Gene Ther. 5:19–28, 1994.*
Allioli et al., "Use of retroviral vectors to introduce and express the β–galactosidase marker gene in cultured chicken primordial germ cells," *Development Biology*, 165:30–37 (1994).
Archer et al., "Human growth hormone (hGH) secretion in milk of goats after direct transfer of the hGH gene into the mammary gland by using replication–defective retrovirus vectors," *Proc. Natl. Acad. Sci. USA*, 91:6840–6844 (1994).
Bayley et al., "Exchange of gene activity in transgenic plants catalyzed by the Cre–lox site–specific recombination system," *Plant Molecular Biology*, 18:353–361 (1992).
Beato, M., "Gene regulation by steroid hormones," *Cell*, 56:335–344 (1989).
Bonifer et al., "Tissue specific and position independant expression of the complete gene domain for chicken lysozyme in transgenic mice," *The EMBO Journal*, 9:2843–2848 (1990).
Bosselman et al., "Germline transmission of exogenous genes in the chicken," *Science*, 243:533–535 (1989).
Brazolot et al., "Efficient transfection of chicken cells by lipofection, and introduction of transfected blastodermal cells into the embryo," *Molecular Reproduction and Development*, 30:304–312 (1991).
Briskin et al., "Heritable retroviral transgenes are highly expressed in chickens," *Proc. Natl. Acad. Sci. USA*, 88:1736–1740 (1991).
Brown et al., "Conformational alterations in the proximal portion of the yeast invertase signal peptide do not block secretion," *Mol. Gen. Genet.*, 197:351–357 (1984).
Burns et al., "Vesicular stomatitis virus G glycoprotein pseudotyped retroviral vectors: Concentration to very high titer and efficient gene transfer into mammalian and non-mammalian cells," *Proc. Natl. Acad. Sci. USA*, 90:8033–8037 (1993).
Chung et al., "A 5' element of the chicken β–globin domain serves as an insulator in human erythroid cells and protects against position effect in drosophila," *Cell*, 74:505–514 (1993).
Cosset et al., "Improvement of avian leukosis virus (ALV)–based retrovirus vectors by using different cis–acting sequences from ALVs," *Journal of Virology*, 85:3388–3394 (1991).
Cosset et al., "Use of helper cells with two host ranges to generate high–titer retroviral vectors," *Virology*, 193:385–395 (1993).
Dean et al., "Regulation of th chicken ovalbumin gene by estrogen and corticosterone requires a novel DNA element that binds a labile protein, chirp–I," *Molecular and Cellular Biology*, 16:2015–2024 (1996).

(List continued on next page.)

Primary Examiner—Jeffrey Fredman
Assistant Examiner—Sumesh Kauahal
(74) *Attorney, Agent, or Firm*—Townsend and Townsend and Crew LLP

(57) ABSTRACT

This invention provides vectors and methods for the stable introduction of exogenous nucleic acid sequences into the genome of a bird and for expressing said exogenous sequences to alter the phenotype of the bird or to produce desired proteins. In particular, transgenic chickens are produced which express exogenous sequences in their oviducts. Eggs which contain exogenous proteins are also produced.

7 Claims, 12 Drawing Sheets

OTHER PUBLICATIONS

Dierich et al., "Cell–specificity of the chicken ovalbumin and conalbumin promoters," *The EMBO Journal*, 6:2305–2312 (1987).

Dugaiczyk et al., "The ovalbumin gene: cloning and molecular organization of the entire natural gene," *Proc. Natl. Acad. Sci. USA*, 76:2253–2257 (1979).

Etches et al., "Contributions to somatic and germline lineages of chicken blastodermal cells maintained in culture," *Molecular Reproduction and Development*, 45:291–298 (1996).

Fisher et al., "Expression of exogenous protein and analysis of morphogenesis in the developing chicken heart using an adenoviral vector," *Carciovascular Research*, 31:E86–E95 (1996).

Gannon et al., "Organisation and sequences at the 5' end of a cloned complete ovalbumin gene," *Nature*, 278:428–434 (1979).

Gu et al., "Deletion of a DNA polymerase β gene segment in T cells using cell type–specific gene targeting," *Science*, 265:103–106 (1994).

Haecker et al., "Repression of the ovalbumin gene involves multiple negative elements including a ubiquitous transcriptional silencer," *Molecular Endocrinology*, 9:1113–1126 (1995).

Johnson et al., "pXeX, a vector for efficient expression of cloned sequences in Xenopus embryos," *Gene*, 147:223–226 (1994).

Kato et al., "A far upstream estrogen response element of the ovalbumin gene contains several half–palindromic 5'–TGACC–3' motifs acting synergistically," *Cell*, 68:731–742 (1992).

Kaye et al., "A close association between sites of Dnase I hypersensitivity and sites of enhanced cleavage by micrococcal nuclease in the 5'–flanking region of the actively transcribed ovalbumin gene," *The EMBO Journal*, 3:1137–1144 (1984).

Lai et al., "The ovalbumin gene: structural sequences in native chicken DNA are not contiguous," *Proc. Natl. Acad. Sci. USA*, 75:2205–2209 (1978).

Lin et al., "Integration and germ–like transmission of a pseudotyped retroviral vector in zebrafish," *Science*, 265:666–669 (1994).

Lobe et al., "Conditioned genome alteration in mice," *BioEssays*, 20:200–208 (1998).

Logie et al., "Ligand–regulated site–specific recombination," *Proc. Natl. Acad. Sci. USA*, 92:5940–5944 (1995).

Lou et al., "Adenovirus–mediated gene transfer into tendon and tendon sheath," *Journal of Orthopaedic Research*, 14:513–517 (1996).

Love et al., "Transgenic birds by DNA microinjection," *Bio/Technology*, 12:60–63 (1994).

Moore et al., "The development of β–lactamase as a highly versatile genetic reporter for eukaryotic cells," *Analytical Biochemistry*, 247:203–209 (1997).

Mountford et al., "Dicistronic targeting constructs: reports and modifiers of mammalian gene expression," *Proc. Natl. Acad. Sci. USA*, 91:4303–4307 (1994).

Nordstrom et al., "A complex array of double–stranded and single–stranded DNA–binding proteins mediates induction of the ovalbumin gene by steroid hormones," *The Journal of Biological Chemistry*, 268:13193–13202 (1993).

Ochiai et al., "Synthesis of human erythropoietin in vivo in the oviduct of laying hens by localized in vivo gene transfer using electroporation," *Poultry Science*, 77:299–302 (1998).

Odell et al., "Seed–specific gene activation mediated by the cre/lox site–specific recombination system," Plant Physiol., 106:447–458 (1994).

Otten et al., "The MMTV LTR promoter is induced by progesterone and dihydrostestosterone but not by estrogen," *Molecular Endocrinology*, 2:143–147 (1988).

Palmiter, R.D., "Quantitation of parameters that determine the rate of ovalbumin synthesis," *Cell*, 4:189–197 (1975).

Palmiter, R.D., "Rate of ovalbumin messenger ribonucleic acid synthesis in the oviduct of estrogen–primed chicks," *The Journal of Biological Chemistry*, 248:8260–8270 (1973).

Park et al., "Modulation of transcriptional activity of the chick ovalbumin gene promoter in primary cultures of chicken oviduct cells: effects of putative regulatory elements in the 5'–flanking region," *Biochemistry and Molecular Biology International*, 36:811–816 (19950.

Roop et al., "Definition of the 5' and 3' ends of transcripts of the ovalbumin gene," 19:63–68 (1980).

Royal et al., "The ovalbumin gene region: common features in the organisation of three genes expressed in chicken oviduct under hormonal control," *Nature*, 279:324–331 (1997).

Rucker et al., "Cre–mediated recombination at the murine whey acidic protein (mWAP) locus," *Molecular Reproduction and Development*, 48:324–331 (1997).

Sanders et al., "Positive and negative regulatory elements control the steroid–responsive ovalbumin promoter," *Biochemistry*, 27:6550–6557 (1988).

Sauer, B., "Manipulation of transgenes by site–specific recombination: use of cre recombinase," *Methods in Enzymology*, 225:890–900 (1993).

Schweers et al., "A protein with a binding specificity similar to NF–$_\kappa$B binds to a steroid–dependent regulatory element in the ovalbumin gene," *The Journal of Biological Chemistry*, 266:10490–10497 (1991).

Thoraval et al., "Germline transmission of exogenous genes in chickens using helper–free ecotropic avian leukosis virus––based vectors," *Transgenic Research*, 4:369–376 (1995).

Uyeda et al., "Cloning and sequencing of hen magnum cDNAs encoding vitelline membrane outer layer protein I (VMO–I)," *Gene*, 144:311–312 (1994).

Vick et al., "Transgenic birds from transformed primordial germ cells," *Proc. R. Soc. Lond. B*, 179–183 (1993).

Yee et al., "Generation of high–titer pseudotyped retroviral vectors with very broad host range," *Methods in Cell Biology*, 43:99–112 (1994).

Zhang et al., "Inducible site–directed recombination in mouse embryonic stem cells," *Nucleic Acids Research*, 24:543–548 (1996).

Zolotukhin et al., "A "humanized" green fluorescent protein cDNA adapted for high–level expression in mammalian cells," *Journal of Virology*, 70:4646–4654 (1996).

Deeley et al., "Synthesis and Deposition of Egg Proteins," eds. Robert J. Etches, Ph.D., D.Sc. and Ann M. Verrinder Gibbins, Ph.D., *Manipulation of the Avian Genome*, Boca Raton, CRC Press(1993), p. 205.

* cited by examiner

OV-1.4 & -7.4: ovalbumin -1.4 and -7.4 kb promoters
gene X: a gene or cDNA encoding an exogenous protein
3' utr: 3' untranslated region containing polyadenylation site
ef-1α: translation elongation factor ef-1α promoter
GFP: humanized green fluorescent protein gene
Ins: 1.2 kb insulator element ↱ transcription start site
5' & 3' LTR: ALV long terminal repeats
Ψ virus packaging signal
Neo: neomycin-reistance gene
OV-1.4: ovalbumin -1.4 kb promoter
LSP: lysozyme signal peptide
gene X: gene or cDNA encoding an exogenous protein 3'utr: 3' untranslated region containing polyadenylation site Same vector as A lacking LSP element Same vector as B lacking LSP element

Lysozyme Signal Peptide

```
            M   G   S   L   L   I   L   V   L   C   F   L   P   L   A
         NcoI                                                    NheI
     51  CCACCATGGG GTCTTTGCTA ATCTTGGTGC TTTGCTTCCT GCCGCTAGCT
         GGTGGTACCC CAGAAACGAT TAGAACCACG AAACGAAGGA CGGCGATCGA

A   L   G▼
         Bsu36I      XbaI              ▼ : Signal peptide cleavage site.
    101  GCCTTAGGGC CCTCTAGAG
         CGGAATCCCG GGAGATCTC
```

PCR Cloning of cDNA

SEQUENCE LISTING

<160> NUMBER OF SEQ ID NOS: 2

<210> SEQ ID NO 1
<211> LENGTH: 69
<212> TYPE: DNA
<213> ORGANISM: Lysozyme signal sequence
<220> FEATURE:
<221> NAME/KEY: CDS
<222> LOCATION: (6)..(59)
<223> OTHER INFORMATION:

<400> SEQUENCE: 1

```
ccacc atg ggg tct ttg cta atc ttg gtg ctt tgc ttc ctg ccg cta gct       50
      Met Gly Ser Leu Leu Ile Leu Val Leu Cys Phe Leu Pro Leu Ala
      1               5                   10                  15 gcc tta ggg ccctctagag                                                  69
Ala Leu Gly
```

<210> SEQ ID NO 2
<211> LENGTH: 18
<212> TYPE: PRT
<213> ORGANISM: Lysozyme signal sequence

```
-continued

<400> SEQUENCE: 2

Met Gly Ser Leu Leu Ile Leu Val Leu Cys Phe Leu Pro Leu Ala Ala
1               5                   10                  15

Leu Gly
```

VECTORS IN AVIAN TRANSGENESIS

This application claims priority from U.S. provisional application Ser. No. 60/062,172, filed Oct. 16, 1997, under 35 USC 119(e)(1).

BACKGROUND OF THE INVENTION a) Field of the Invention

The present invention relates to vectors and methods for the introduction of exogenous genetic material into avian cells and the expression of the exogenous genetic material in the cells. The invention also relates to transgenic avian species, including chickens, and to avian eggs which contain exogenous protein.

b) Description of Related Art

Numerous natural and synthetic proteins are used in diagnostic and therapeutic applications; many others are in development or in clinical trials. Current methods of protein production include isolation from natural sources and recombinant production in bacterial and mammalian cells. Because of the complexity and high cost of these methods of protein production, however, efforts are underway to develop alternatives. For example, methods for producing exogenous proteins in the milk of pigs, sheep, goats, and cows have been reported. These approaches suffer from several limitations, including long generation times between founder and production transgenic herds, extensive husbandry and veterinary costs, and variable levels of expression because of position effects at the site of the transgene insertion in the genome. Proteins are also being produced using milling and malting processes from barley and rye. However, plant post-translational modifications differ from vertebrate post-translational modifications, which often has a critical effect on the function of the exogenous proteins.

Like tissue culture and mammary gland bioreactors, the avian oviduct can also potentially serve as a bioreactor. Successful methods of modifying avian genetic material such that high levels of exogenous proteins are secreted in and packaged into eggs would allow inexpensive production of large amounts of protein. Several advantages of such an approach would be: a) short generation times (24 weeks) and rapid establishment of transgenic flocks via artificial insemination; b) readily scaled production by increasing flock sizes to meet production needs; c) post-translational modification of expressed proteins; 4) automated feeding and egg collection; d) naturally sterile egg-whites; and e) reduced processing costs due to the high concentration of protein in the egg white.

The avian reproductive system, including that of the chicken, is well described. The egg white of the hen consists of several layers which are secreted upon the yolk during its passage through the oviduct. The production of an egg begins with formation of the large yolk in the ovary of the hen. The unfertilized oocyte is positioned on top of the yolk sac. Upon ovulation or release of the yolk from the ovary, the oocyte passes into the infindibulum of the oviduct where it is fertilized if sperm are present. It then moves into the magnum of the oviduct which is lined with tubular gland cells. These cells secrete the egg-white proteins, including ovalbumin, lysozyme, ovomucoid, conalbumin, and ovomucin, into the lumen of the magnum where they are deposited onto the avian embryo and yolk.

The ovalbumin gene encodes a 45 kD protein that is specifically expressed in the tubular gland cells of the magnum of the oviduct (Beato, *Cell* 56:335–344 (1989)). Ovalbumin is the most abundant egg white protein, comprising over 50 percent of the total protein produced by the tubular gland cells, or about 4 grams of protein per large Grade A egg (Gilbert, "Egg albumen and its formation" in *Physiology and Biochemistry of the Domestic Fowl*, Bell and Freeman, eds., Academic Press, London, New York, pp. 1291–1329). The ovalbumin gene and over 20 kb of each flanking region have been cloned and analyzed (Lai et al., *Proc. Natl. Acad Sci. USA* 75:2205–2209 (1978); Gannon et al., *Nature* 278:428–424 (1979); Roop et al., *Cell* 19:63–68 (1980); and Royal et al., *Nature* 279:125–132 (1975)).

Much attention has been paid to the regulation of the ovalbumin gene. The gene responds to steroid hormones such as estrogen, glucocorticoids, and progesterone, which induce the accumulation of about 70,000 ovalbumin mRNA transcripts per tubular gland cell in immature chicks and 100,000 ovalbumin mRNA transcripts per tubular gland cell in the mature laying hen (Palmiter, *J Biol. Chem.* 248:8260–8270 (1973); Palmiter, *Cell* 4:189–197 (1975)). DNAse hypersensitivity analysis and promoter-reporter gene assays in transfected tubular gland cells defined a 7.4 kb region as containing sequences required for ovalbumin gene expression. This 5' flanking region contains four DNAse I-hypersensitive sites centered at −0.25, −0.8, −3.2, and −6.0 kb from the transcription start site. These sites are called HS-I, -II, -III, and -IV, respectively. These regions reflect alterations in the chromatin structure and are specifically correlated with ovalbumin gene expression in oviduct cells (Kaye et al., *EMBO* 3:1137–1144 (1984)). Hypersensitivity of HS-II and -III are estrogen-induced, supporting a role for these regions in hormone-induction of ovalbumin gene expression.

HS-I and HS-II are both required for steroid induction of ovalbumin gene transcription, and a 1.4 kb portion of the 5' region that includes these elements is sufficient to drive steroid-dependent ovalbumin expression in explanted tubular gland cells (Sanders and McKnight, *Biochemistry* 27: 6550–6557 (1988)). HS-I is termed the negative-response element ("NRE") because it contains several negative regulatory elements which repress ovalbumin expression in the absence of hormone (Haekers et al., *Mol. Endo.* 9:1113–1126 (1995)). Protein factors bind these elements, including some factors only found in oviduct nuclei suggesting a role in tissue-specific expression. HS-II is termed the steroid-dependent response element ("SDRE") because it is, required to promote steroid induction of transcription. It binds a protein or protein complex known as Chirp-I. Chirp-I is induced by estrogen and turns over rapidly in the presence of cyclohexamide (Dean et al., *Mol. Cell. Biol.* 16:2015–2024 (1996)): Experiments using an explanted tubular gland cell culture system defined an additional set of factors that bind SDRE in a steroid-dependent manner, including a NFκB-like factor (Nordstrom et al., *J Biol. Chem.* 268:13193–13202 (1993); Schweers and Sanders, *J Biol. Chem.* 266: 10490–10497 (1991)).

Less is known about the function of HS-III and -IV. HS-III contains a functional estrogen response element, and confers estrogen inducibility to either the ovalbumin proximal promoter or a heterologous promoter when co-transfected into HeLa cells with an estrogen receptor cDNA. These data imply that HS-111 may play a functional role in the overall regulation of the ovalbumin gene. Little is known about the function of HS-IV, except that it does not contain a functional estrogen-response element (Kato et al., *Cell* 68: 731–742 (1992)).

There has been much interest in modifying eukaryotic genomes by introducing foreign genetic material and/or by disrupting specific genes. Certain eukaryotic cells may prove to be superior hosts for the production of exogenous eukaryotic proteins. The introduction of genes encoding certain proteins also allows for the creation of new phenotypes which could have increased economic value. In addition, some genetically-caused disease states may be cured by the introduction of a foreign gene that allows the genetically defective cells to express the protein that it can otherwise not produce. Finally, modification of animal genomes by insertion or removal of genetic material permits basic studies of gene function, and ultimately may permit the introduction of genes that could be used to cure disease states, or result in improved animal phenotypes.

Transgenesis has been accomplished in mammals by several different methods. First, in mammals including the mouse, pig, goat, sheep and cow, a transgene is microinjected into the pronucleus of a fertilized egg, which is then placed in the uterus of a foster mother where it gives rise to a founder animal carrying the transgene in its germline. The transgene is engineered to carry a promoter with specific regulatory sequences directing the expression of the foreign protein to a particular cell type. Since the transgene inserts randomly into the genome, position effects at the site of the transgene's insertion into the genome may variably cause decreased levels of transgene expression. This approach also requires characterization of the promoter such that sequences necessary to direct expression of the transgene in the desired cell type are defined and included in the transgene vector (Hogan et al. *Manipulating the Mouse Embryo*, Cold Spring Harbor Laboratory, N.Y. (1988)).

A second method for effecting animal transgenesis is targeted gene disruption, in which a targeting vector bearing sequences of the target gene flanking a selectable marker gene is introduced into embryonic stem ("ES") cells. Via homologous recombination, the targeting vector replaces the target gene sequences at the chromosomal locus or inserts into interior sequences preventing expression of the target gene product. Clones of ES cells bearing the appropriately disrupted gene are selected and then injected into early stage blastocysts generating chimeric founder animals, some of which bear the transgene in the germ line. In the case where the transgene deletes the target locus, it replaces the target locus with foreign DNA borne in the transgene vector, which consists of DNA encoding a selectable marker useful for detecting transfected ES cells in culture and may additionally contain DNA sequences encoding a foreign protein which is then inserted in place of the deleted gene such that the target gene promoter drives expression of the foreign gene (U.S. Pat. Nos. 5,464,764 and 5,487,992 (M. P. Capecchi and K. R. Thomas)). This approach suffers from the limitation that ES cells are unavailable in many mammals, including goats, cows, sheep and pigs. Furthermore, this method is not useful when the deleted gene is required for survival or proper development of the organism or cell type.

Recent developments in avian transgenesis have allowed the modification of avian genomes. Germ-line transgenic chickens may be produced by injecting replication-defective retrovirus into the subgerminal cavity of chick blastoderms in freshly laid eggs (U.S. Pat. No. 5,162,215; Bosselman et al., *Science* 243:533–534 (1989); Thoraval et al., *Transgenic Research* 4:369–36 (1995)). The retroviral nucleic acid carrying a foreign gene randomly inserts into a chromosome of the embryonic cells, generating transgenic animals, some of which bear the transgene in their germ line. Unfortunately, retroviral vectors cannot harbor large pieces of DNA, limiting the size and number of foreign genes and foreign regulatory sequences that may be introduced using this method. In addition, this method does not allow targeted introduction or disruption of a gene by homologous recombination. Use of insulator elements inserted at the 5' or 3' region of the fused gene construct to overcome position effects at the site of insertion has been described (Chim et al., *Cell* 74:504–514 (1993)).

In another approach, a transgene has been microinjected into the germinal disc of a fertilized egg to produce a stable transgenic founder bird that passes the gene to the F1 generation (Love et al. *Bio/Technology* 12:60–63 (1994)). This method has several disadvantages, however. Hens must be sacrificed in order to collect the fertilized egg, the fraction of transgenic founders is low, and injected eggs require labor intensive in vitro culture in surrogate shells.

In another approach, blastodermal cells containing presumptive primordial germ cells ("PGCs") are excised from donor eggs, transfected with a transgene and introduced into the subgerminal cavity of recipient embryos. The transfected donor cells are incorporated into the recipient embryos generating transgenic embryos, some of which are expected to bear the transgene in the germ line. The transgene inserts in random chromosomal sites by nonhomologous recombination. This approach requires characterization of the promoter such that sequences necessary to direct expression of the transgene in the desired cell type are defined and included in the transgene vector. However, no transgenic founder birds have yet been generated by this method.

A targeting vector containing flanking DNA sequences of the vitellogenin gene has been used to delete part of the resident gene in chicken blastodermal cells in culture. However, it has not been demonstrated that these cells can contribute to the germ line and thus produce a transgenic embryo. In addition, this method is not useful when the deleted gene is required for survival or proper development of the organism or cell type.

Thus, it can be seen that there is a need for a method of introducing foreign DNA which is operably linked to a magnum-active promoter into the avian genome. There is also a need for a method of introducing foreign DNA into nonessential portions of a target gene of the avian genome such that the target gene's regulatory sequences drive expression of the foreign DNA, preferably without disrupting the function of the target gene. The ability to effect expression of the integrated transgene selectively within the avian oviduct is also desirable. Furthermore, there exists a need to create germ-line modified transgeneic birds which express exogenous genes in their oviducts and secrete the expressed exogenous proteins into their eggs.

SUMMARY OF THE INVENTION

This invention provides methods for the stable introduction of exogenous coding sequences into the genome of a bird and expressing those exogenous coding sequences to produce desired proteins or to alter the phenotype of the bird. Synthetic vectors useful in the methods are also provided by the present invention, as are transgenic birds which express exogenous protein and avian eggs containing exogenous protein.

In one embodiment, the present invention provides methods for producing exogenous proteins in specific tissues of avians. In particular, the invention provides methods of producing exogenous proteins in an avian oviduct. Transgenes are introduced into embryonic blastodermal cells, preferably near stage X, to produce a transgenic bird, such that the protein of interest is expressed in the tubular gland cells of the magnum of the oviduct, secreted into the lumen, and deposited onto the egg yolk. A transgenic bird so produced carries the transgene in its germ line. The exogenous genes can therefore be transmitted to birds by both artificial introduction of the exogenous gene into bird embryonic cells, and by the transmission of the exogenous gene to the bird's offspring stably in a Mendelian fashion.

The present invention provides for a method of producing an exogenous protein in an avian oviduct. The method comprises as a first step providing a vector that contains a coding sequence and a promoter operably linked to the coding sequence, so that the promoter can effect expression of the nucleic acid in the tubular gland cells of the magnum of an avian oviduct. Next, the vector is introduced into avian embryonic blastodermal cells, either freshly isolated, in culture, or in an embryo, so that the vector sequence is randomly inserted into the avian genome. Finally, a mature transgenic avian which expresses the exogenous protein in its oviduct is derived from the transgenic blastodermal cells. This method can also be used to produce an avian egg which contains exogenous protein when the exogenous protein that is expressed in the tubular gland cells is also secreted into the oviduct lumen and deposited onto the yolk of an egg.

In one embodiment, the production of a transgenic bird by random chromosomal insertion of a vector into its avian genome may optionally involve DNA transfection of embryonic blastodermal cells which are then injected into the subgerminal cavity beneath a recipient blastoderm. The vector used in such a method has a promoter which is fused to an exogenous coding sequence and directs expression of the coding sequence in the tubular gland cells of the oviduct.

In an alternative embodiment, random chromosomal insertion and the production of a transgenic bird is accomplished by transduction of embryonic blastodermal cells with replication-defective or replication-competent retroviral particles carrying transgene RNA between the 5' and 3' LTRs of the retroviral vector. For instance, in one specific embodiment, an avian leukosis virus (ALV) retroviral vector is used which comprises a modified pNLB plasmid containing an exogenous gene that is inserted downstream of a segment of the ovalbumin promoter region. An RNA copy of the modified retroviral vector, packaged into viral particles, is used to infect embryonic blastoderms which develop into transgenic birds. Alternatively, helper cells which produce the retroviral transducing particles are delivered to the embryonic blastoderm.

In one embodiment, the vector used in the methods of the invention contains a promoter which is magnum-specific. In this embodiment, expression of the exogenous coding sequence occurs only in the oviduct. Optionally, the promoter used in this embodiment may be a segment of the ovalbumin promoter region. One aspect of the invention involves truncating the ovalbumin promoter and/or condensing the critical regulatory elements of the ovalbumin promoter so that it retains sequences required for high levels of expression in the tubular gland cells of the magnum of the oviduct, while being small enough that it can be readily incorporated into vectors. For instance, a segment of the ovalbumin promoter region may be used. This segment comprises the 5'-flanking region of the ovalbumin gene. The total length of the ovalbumin promoter segment may be from about 0.88 kb to about 7.4 kb in length, and is preferably from about 0.88 kb to about 1.4 kb in length. The segment preferably includes both the steroid-dependent regulatory element and the negative regulatory element of the ovalbumin gene. The segment optionally also includes residues from the 5' untranslated region (5' UTR) of the ovalbumin gene. In an alternative embodiment, the magnum-specific promoter may be a segment of the promoter region of the conalbumin, ovomucoid, or ovomucin genes.

In another embodiment of the invention, the vectors integrated into the avian genome contain constitutive promoters which are operably linked to the exogenous coding sequence. Alternatively, the promoter used in the expression vector may be derived from that of the lysozyme gene, a gene expressed in both the oviduct and macrophages.

If a constitutive promoter is operably linked to an exogenous coding sequence which is to be expressed in the oviduct, then the methods of the invention may also optionally involve providing a second vector which contains a second coding sequence and a magnum-specific promoter operably linked to the second coding sequence. This second vector is also expressed in the tubular gland cells of the mature transgenic avian. In this embodiment, expression of the first coding sequence in the magnum is directly or indirectly dependent upon the cellular presence of the protein expressed by the second vector. Such a method may optionally include the use of a Cre-loxP system.

In an alternative embodiment, the production of the transgenic bird is accomplished by homologous recombination of the transgene into a specific chromosomal locus. An exogenous promoter-less minigene is inserted into the target locus, or endogenous gene, whose regulatory sequences then govern the expression of the exogenous coding sequence. This technique, promoter-less minigene insertion (PMGI), is not limited to use with target genes directing oviduct-specific expression, and may therefore be used for expression in any organ when inserted into the appropriate locus. In addition to enabling the production of exogenous proteins in eggs, the promoter-less minigene insertion method is amenable to applications in the poultry production and egg-laying industries where gene insertions may enhance critical avian characteristics such as muscling, disease resistance, and livability or to reduce egg cholesterol.

One aspect of the present invention provides for a targeting vector which may be used for promoter-less minigene insertion into a target endogenous gene in an avian. This vector includes a coding sequence, at least one marker gene, and targeting nucleic acid sequences. The marker gene is operably linked to a constitutive promoter, such as the *Xenopus laevis* ef-1α promoter, the HSV tk promoter, the CMV promoter, and the β-actin promoter, and can be used for identifying cells which have integrated the targeting vector. The targeting nucleic acid sequences correspond to the sequences which flank the point of insertion in the target gene, and then direct insertion of the targeting vector into the target gene.

The present invention provides for a method of producing an exogenous protein in specific cells in an avian. The method involves providing a targeting vector containing the promoter-less minigene. The targeting vector is designed to target an endogenous gene that is expressed in the specific cells into avian embryonic blastodermal cells. The transgenic embryonic blastodermal cells are then injected into the subgerminal cavity beneath a recipient blastoderm or otherwise introduced into avian embryonic blastodermal cells. The targeting vector is integrated into the target endogenous gene. The resulting bird then expresses the exogenous coding sequence under the control of the regulatory elements of the target gene in the desired avian cells. This method may also be used for producing an avian egg that contains exogenous protein if a mature transgenic bird is ultimately derived from the transgenic embryonic blastodermal cells. In the transgenic bird, the coding sequence is expressed in the magnum under the control of the regulatory sequences of a target gene, and the exogenous protein is secreted into the oviduct lumen, so that the exogenous protein is deposited onto the yolk of an egg laid by the bird.

In one embodiment of the invention, the targeted endogenous gene is a gene expressed in the tubular gland cells of the avian oviduct. A preferred target endogenous gene for selective expression in the tubular gland cells is the ovalbumin gene (OV gene). While the invention is primarily exemplified via use of the ovalbumin gene as a target endogenous gene, other suitable endogenous genes may be used. For example, conalbumin, ovomucoid, ovomucin, and lysozyme may all be used as target genes for the expression of exogenous proteins in tubular gland cells of an avian oviduct in accordance with the invention.

The point of insertion in a method involving promoter-less minigene insertion may be in the 5' untranslated region of the target gene. Alternatively, if the targeting vector used for the insertion contains an internal ribosome entry element directly upstream of the coding sequence, then the point of insertion may be in the 3' untranslated region of the target gene.

Another aspect of the invention provides for an avian egg which contains protein exogenous to the avian species. Use of the invention allows for expression of exogenous proteins in oviduct cells with secretion of the proteins into the lumen of the oviduct magnum and deposition upon the yolk of the avian egg. Proteins thus packaged into eggs may be present in quantities of up to one gram or more per egg.

Other embodiments of the invention provide for transgenic birds, such as chickens or turkeys, which carry a transgene in the genetic material of their germ-line tissue. In one embodiment, the transgene comprises an exogenous gene operably linked to a promoter which optionally may be magnum-specific. In this transgenic bird the exogenous gene is expressed in the tubular gland cells of the oviduct. In an alternative embodiment, the transgene instead comprises an exogenous gene which is positioned in either the 5' untranslated region or the 3' untranslated region of an endogenous gene in a manner that allows the regulatory sequences of the endogenous gene to direct expression of the exogenous gene. In this embodiment, the endogenous gene may optionally be ovalbumin, lysozyme, conalbumin, ovomucoid, or ovomucin.

BRIEF DESCRIPTION OF THE DRAWINGS

In FIG. 6(b), schematic cre recombinase and β-lactamase transgenes are shown integrated into the genome of a hen in a magnum cell.

Figure 1A:
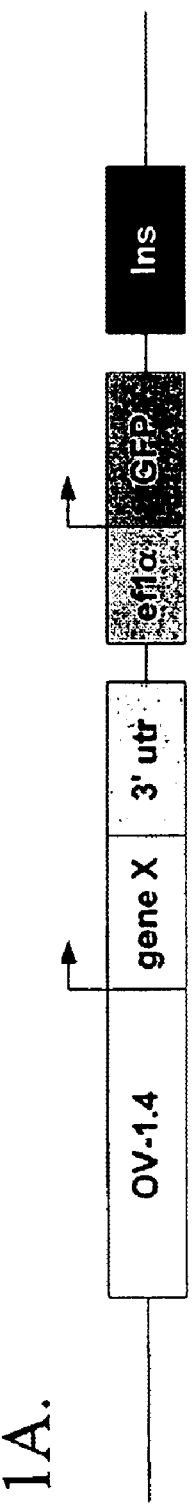
FIGS. 1(a) and 1(b) illustrate ovalbumin promoter expression vectors comprising ovalbumin promoter segments and a coding sequence, gene X which encodes an exogenous protein X.

DETAILED DESCRIPTION OF THE INVENTION a) Definitions and General Parameters

The following definitions are set forth to illustrate and define the meaning and scope of the various terms used to describe the invention herein.

A "nucleic acid or polynucleotide sequence" includes, but is not limited to, eucaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence. A coding sequence may be flanked on the 5' and/or 3' ends by untranslated regions.

"Exon" refers to that part of a gene which, when transcribed into a nuclear transcript, is "expressed" in the cytoplasmic mRNA after removal of the introns or intervening sequences by nuclear splicing.

Nucleic acid "control sequences" or "regulatory sequences" refer to translational start and stop codons, promoter sequences, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eucaryotic cells are promoters, polyadenylation signals, and enhancers. All of these control sequences need not be present in a recombinant vector so long as those necessary and sufficient for the transcription and translation of the desired gene are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct tip could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

"Exogenous protein" as used herein refers to a protein not naturally present in a particular tissue or cell, a protein that is the expression product of an exogenous expression construct or transgene, or a protein not naturally present in a given quantity in a particular tissue or cell.

"Endogenous gene" refers to a naturally occurring gene or fragment thereof normally associated with a particular cell.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro, or in vivo, the latter being performed by a host cell through posttaanslational processing systems. Such modifications may increase or decrease the biological activity of the molecule, and such chemically modified molecules are also intended to come within the scope of the invention.

Alternative methods of cloning, amplification, expression, and purification will be apparent to the skilled artisan. Representative methods are disclosed in Sambrook, Fritsch, and Maniatis, *Molecular Cloning, a Laboratory Manual*, 2nd Ed., Cold Spring Harbor Laboratory (1989).

"PMGI" refers to promoter-less minigene insertion, a method in which a gene lacking a promoter is inserted via homologous recombination into a target gene such that the target gene's regulatory sequences govern the expression of the inserted gene in an appropriate tissue. A minigene is a modified version of a gene, often just a cDNA with an appropriate polyadenylation signal and sometimes an intron. A minigene usually lacks all of the introns of the genomic gene.

"Vector" means a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally may be included in the construct, preferably $\geq 100$ bp 5' to the coding sequence.

In some embodiments the promoter will be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box. Enhancer elements can also stimulate transcription from linked promoters, but many function exclusively in a particular cell type. Many enhancer/promoter elements derived from viruses, e.g. the SV40, the Rous sarcoma virus (RSV), and CMV promoters are active in a wide array of cell types, and are termed "constitutive" or "ubiquitous." The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

The termination region which is employed primarily will be one of convenience, since termination regions appear to be relatively interchangeable. The termination region may be native to the intended nucleic acid sequence of interest, or may be derived from another source.

A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "marker gene" is a gene which encodes a protein that allows for identification and isolation of correctly transfected cells. Suitable marker sequences include, but are not limited to green, yellow, and blue fluorescent protein genes (GFP, YFP, and BFP, respectively). Other suitable markers include thymidine kinase (tk), dihydrofolate reductase (DHFR), and aminoglycoside phosphotransferase (APH) genes. The latter imparts resistance to the aminoglycoside antibiotics, such as kanamycin, neomycin, and geneticin. These, and other marker genes such as those encoding chloramphenicol acetyltransferase (CAT), β-lactamase, β-galactosidase (β-gal), may be incorporated into the primary nucleic acid cassette along with the gene expressing the desired protein, or the selection markers may be contained on separate vectors and cotransfected.

A "reporter gene" is a marker gene that "reports" its activity in a cell by the presence of the protein that it encodes.

A "retroviral particle", "transducing particle", or "transduction particle" refers to a replication-defective or replication-competent virus capable of transducing non-viral DNA or RNA into a cell.

The terms "transformation", "transduction" and "transfection" all denote the introduction of a polynucleotide into an avian blastodermal cell.

"Magnum" is that part of the oviduct between the infundibulum and the isthmus containing tubular gland cells that synthesize and secrete the egg white proteins of the egg.

A "magnum-specific" promoter, as used herein, is a promoter which is primarily or exclusively active in the tubular gland cells of the magnum.

b) Transgenesis of Blastodermal Cells

By the methods of the present invention, transgenes can be introduced into avian embryonic blastodermal cells, to produce a transgenic chicken, or other avian species, that carries the transgene in the genetic material of its germ-line tissue. The blastodermal cells are typically stage VII–XII cells, or the equivalent thereof, and preferably are near stage X. The cells useful in the present invention include embryonic germ (EG) cells, embryonic stem (ES) cells & primordial germ cells (PGCs). The embryonic blastodermal cells may be isolated freshly, maintained in culture, or reside within an embryo.

A variety of vectors useful in carrying out the methods of the present invention are described herein. These vectors may be used for stable introduction of an exogenous coding sequence into the genome of a bird. In alternative embodiments, the vectors may be used to produce exogenous proteins in specific tissues of an avian, and in the oviduct in particular. In still further embodiments, the vectors are used in methods to produce avian eggs which contain exogenous protein.

In some cases, introduction of a vector of the present invention into the embryonic blastodermal cells is performed with embryonic blastodermal cells that are either freshly isolated or in culture. The transgenic cells are then typically injected into the subgerminal cavity beneath a recipient blastoderm in an egg. In some cases, however, the vector is delivered directly to the cells of a blastodermal embryo.

In one embodiment of the invention, vectors used for transfecting blastodermal cells and generating random, stable integration into the avian genome contain a coding sequence and a magnum-specific promoter in operational and positional relationship to express the coding sequence in the tubular gland cell of the magnum of the avian oviduct.

The magnum-specific promoter may optionally be a segment of the ovalbumin promoter region which is sufficiently large to direct expression of the coding sequence in the tubular gland cells. For instance, the promoter may be derived from the promoter regions of the ovalbumin, lysozyme, conalbumin, ovomucoid, or ovomucin genes. Alternatively, the promoter may be a promoter that is largely, but not entirely, specific to the magnum, such as the lysozyme promoter.

Figure 1B:
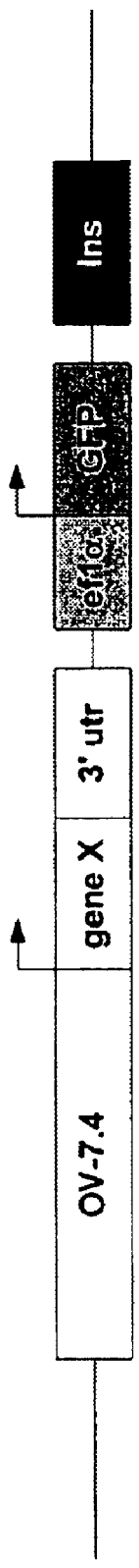

FIGS. 1(a) and 1(b) illustrate examples of ovalbumin promoter expression vectors. Gene X is a coding sequence which encodes an exogenous protein. Bent arrows indicate the transcriptional start sites. In one example, the vector contains 1.4 kb of the 5' flanking region of the ovalbumin gene (FIG. 1(a)). The sequence of the "−1.4 kb promoter" of FIG. 1(a) corresponds to the sequence starting from approximately 1.4 kb upstream (−1.4 kb) of the ovalbumin transcription start site and extending approximately 9 nucleotides into the 5' untranslated region of the ovalbumin gene. The approximately 1.4 kb-long segment harbors two critical regulatory elements, the steroid-dependent regulatory element (SDRE) and the negative regulatory element (NRE). The NRE is so named because it contains several negative regulatory elements which block the gene's expression in the absence of hormone. A shorter 0.88 kb segment also contains both elements. In another example, the vector contains approximately 7.4 kb of the 5' flanking region of the ovalbumin gene and harbors two additional elements (HS-III and HS-IV), one of which is known to contain a functional region enabling induction of the gene by estrogen (FIG. 1(b)). A shorter 6 kb segment also contains all four elements and could optionally be used in the present invention.

Each vector used for random integration according to the present invention preferably comprises at least one 1.2 kb element from the chicken β-globin locus which insulates the gene within from both activation and inactivation at the site of insertion into the genome. In a preferred embodiment, two insulator elements are added to one end of the ovalbumin gene construct. In the β-globin locus, the insulator elements serve to prevent the distal locus control region (LCR) from activating genes upstream from the globin gene domain, and have been shown to overcome position effects in transgenic flies, indicating that they can protect against both positive and negative effects at the insertion site. The insulator element(s) are only needed at either the 5' or 3' end of the gene because the transgenes are integrated in multiple, tandem copies effectively creating a series of genes flanked by the insulator of the neighboring transgene. In another embodiment, the insulator element is not linked to the vector but is cotransfected with the vector. In this case, the vector and the element are joined in tandem in the cell by the process of random integration into the genome.

Each vector may optionally also comprise a marker gene to allow identification and enrichment of cell clones which have stably integrated the expression vector. The expression of the marker gene is driven by a ubiquitous promoter that drives high levels of expression in a variety of cell types. In a preferred embodiment the green fluorescent protein (GFP) reporter gene (Zolotukhin et al., *J. Virol* 70:46464654 (1995)) is driven by the Xenopus elongation factor 1-α (ef-1α) promoter (Johnson and Krieg, *Gene* 147:223–26 (1994)). The Xenopus ef-1α promoter is a strong promoter expressed in a variety of cell types. The GFP contains mutations that enhance its fluorescence and is humanized, or modified such that the codons match the codon usage profile of human genes. Since avian codon usage is virtually the same as human codon usage, the humanized form of the gene is also highly expressed in avian blastodermal cells. In alternative embodiments, the marker gene is operably linked to one of the ubiquitous promoters of HSV tk, CMV, or β-actin.

While human and avian codon usage is well matched, where a nonvertebrate gene is used as the coding sequence in the transgene, the nonvertebrate gene sequence may be modified to change the appropriate codons such that codon usage is similar to that of humans and avians.

Transfection of the blastodermal cells may be mediated by any number of methods known to those of ordinary skill in the art. The introduction of the vector to the cell may be aided by first mixing the nucleic acid with polylysine or cationic lipids which help facilitate passage across the cell membrane. However, introduction of the vector into a cell is preferably achieved through the use of a delivery vehicle such as a liposome or a virus. Viruses which may be used to introduce the vectors of the present invention into a blastodermal cell include, but are not limited to, retroviruses, adenoviruses, adeno-associated viruses, herpes simplex viruses, and vaccinia viruses.

In one method of transfecting blastodermal cells, a packaged retroviral-based vector is used to deliver the vector into embryonic blastodermal cells so that the vector is integrated into the avian genome.

As an alternative to delivering retroviral transduction particles to the embryonic blastodermal cells in an embryo, helper cells which produce the retrovirus can be delivered to the blastoderm.

A preferred retrovirus for randomly introducing a transgene into the avian genome is the replication-deficient ALV retrovirus. To produce an appropriate ALV retroviral vector, a pNLB vector is modified by inserting a region of the ovalbumin promoter and one or more exogenous genes between the 5' and 3' long terminal repeats (LTRs) of the retrovirus genome. Any coding sequence placed downstream of the ovalbumin promoter will be expressed at high levels and only in the tubular gland cells of the oviduct magnum because the ovalbumin promoter drives the high level of expression of the ovalbumin protein and is only active in the oviduct tubular gland cells. While a 7.4 kb ovalbumin promoter has been found to produce the most active construct when assayed in cultured oviduct tubular gland cells, the ovalbumin promoter must be shortened for use in the retroviral vector. In a preferred embodiment, the retroviral vector comprises a 1.4 kb segment of the ovalbumin promoter; a 0.88 kb segment would also suffice.

Any of the vectors of the present invention may also optionally include a coding sequence encoding a signal peptide that will direct secretion of the protein expressed by the vector's coding sequence from the tubular gland cells of the oviduct. This aspect of the invention effectively broadens the spectrum of exogenous proteins that may be deposited in avian eggs using the methods of the invention. Where an exogenous protein would not otherwise be secreted, the vector bearing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the cDNA.

Figure 2A:
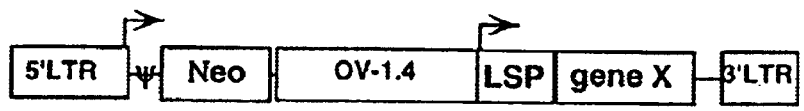
FIGS. 2(a), 2(b), 2(c) and 2(d) illustrate retroviral vectors of the invention comprising an ovalbumin promoter and a coding sequence, gene X, encoding an exogenous protein X.
Figure 2B:
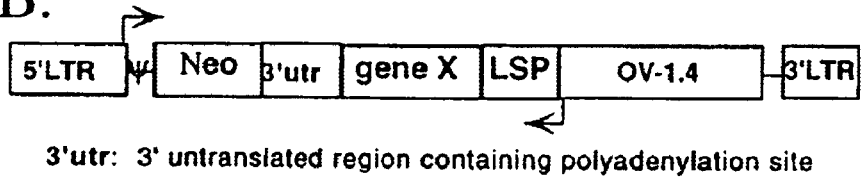
Figure 2C:
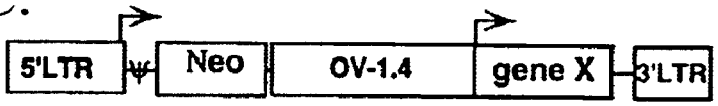
Figure 2D:
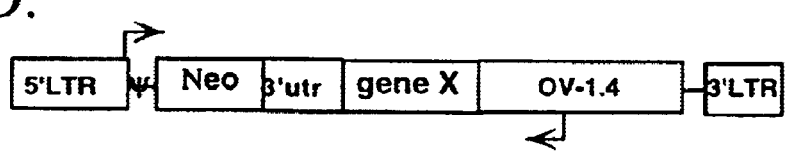

FIGS. 2(a)–2(d), and 2(f) illustrate examples of suitable retroviral vectors. The vector is inserted into the avian genome with 5' and 3' flanking LTRs. Neo is the neomycin phosphotransferase gene. Bent arrows indicate transcription start sites. FIGS. 2(a) and 2(b) illustrate LTR and oviduct transcripts with a sequence encoding the lysozyme signal peptide (LSP), whereas FIGS. 2(c) and 2(d) illustrate transcripts without such a sequence. There are two parts to the retroviral vector strategy. Any protein that contains a eukaryotic signal peptide may be cloned into the vectors depicted in FIGS. 2(b) and 2(d). Any protein that is not ordinarily secreted may be cloned into the vectors illustrated in FIGS. 2(a) and 2(b) to enable its secretion from the tubular gland cells.

Figure 2E:
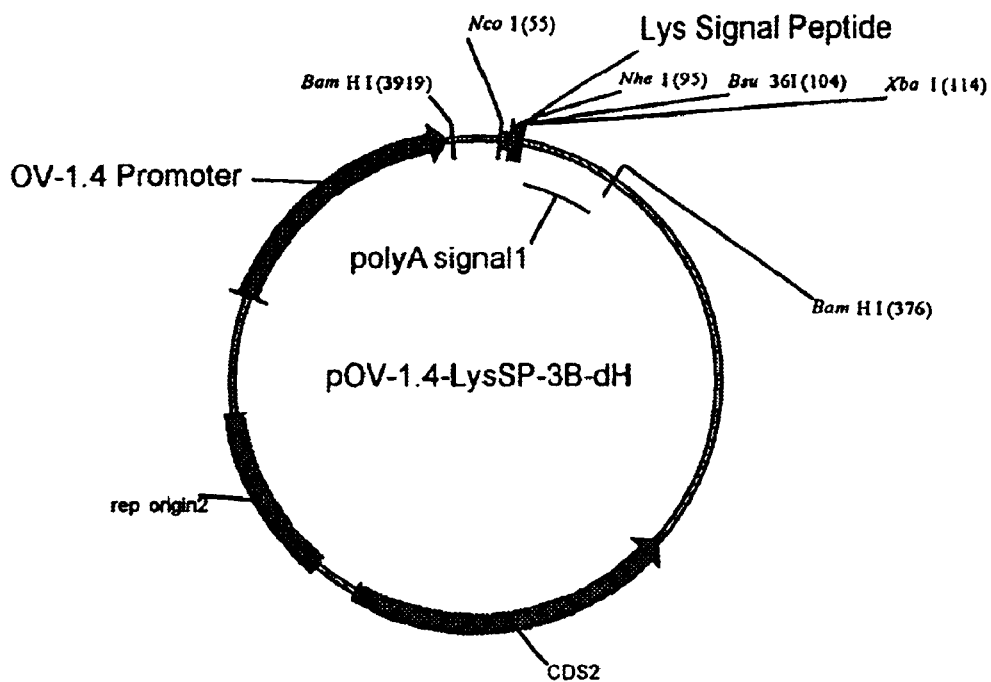
FIG. 2(e) illustrates a method of amplifying an exogenous gene for insertion in to the vectors of 2(a) and 2(b), and defines the lysozyme signal 1)peptide (SEQ ID NOS:1–2), wherein the nucleic acid sequences encoding the lysozyme signal peptide comprises the nucleotide sequences of SEQ NO:1.
Figure 2E:
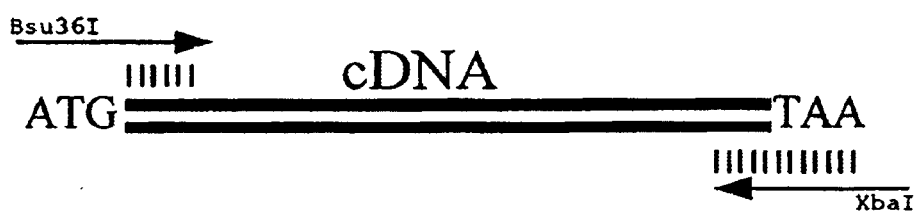

FIG. 2(e) illustrates the strategy for cloning an exogenous gene into a lysozyme signal peptide vector. The polymerase chain reaction is used to amplify a copy of a coding sequence, gene X, using a pair of oligonucleotide primers containing restriction enzyme sites that enable the insertion of the amplified gene into the plasmid after digestion with the two enzymes. The 5' and 3' oligonucleotides contain the Bsu36I and Xba1 restriction sites, respectively.

Another aspect of the invention involves the use of internal ribosome entry site (IRES) elements in any of the vectors of the present invention to allow the translation of two or more proteins from a di- or polycistronic mRNA. The IRES units are fused to 5' ends of one or more additional coding sequences which are then inserted into the vectors at the end of the original coding sequence, so that the coding sequences are separated from one another by an IRES. Pursuant to this aspect of the invention, post-translational modification of the product is facilitated because one coding sequence may encode an enzyme capable of modifying the other coding sequence product. For example, the first coding sequence may encode collagen which would be hydroxylated and made active by the enzyme encoded by the second coding sequence.

Figure 2F:
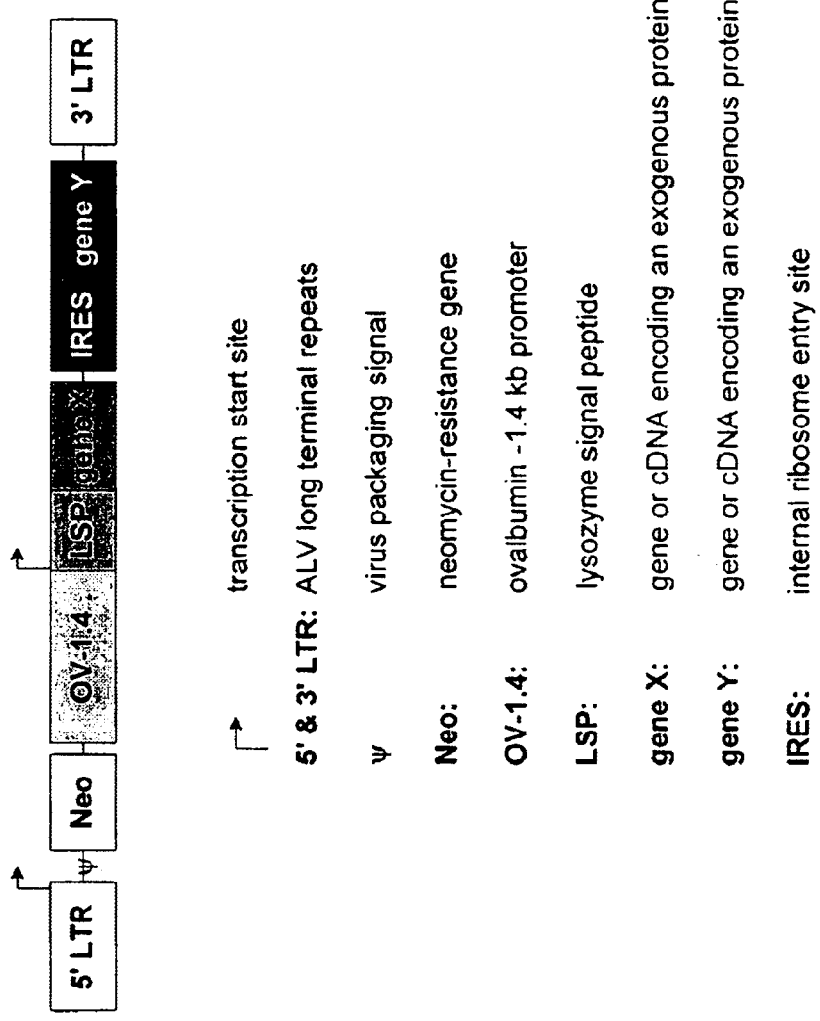
FIG. 2(f) illustrates a retroviral vector comprising an ovalbumin promoter controlling expression of a coding sequence, gene X, and an internal ribosome entry site (IRES) element enabling expression of a second coding sequence, gene Y.

For instance, in the retroviral vector example of FIG. 2(f), an internal ribosome entry site (IRES) element is positioned between two exogenous coding sequences (gene X and gene Y). The IRES allows both protein X and protein Y to be translated from the same transcript directed by the ovalbumin promoter. Bent arrows indicate transcription start sites. The expression of the protein encoded by gene X is expected to be highest in tubular gland cells, where it is specifically expressed but not secreted. The protein encoded by gene Y is also expressed specifically in tubular gland cells but because it is efficiently secreted, protein Y is packaged into the eggs.

In another aspect of the invention, the coding sequences of vectors used in any of the methods of the present invention are provided with a 3' untranslated region (3' UTR) to confer stability to the RNA produced. When a 3' UTR is added to a retroviral vector, the orientation of the fused ovalbumin promoter, gene X and the 3' UTR must be reversed in the construct, so that the addition of the 3' UTR will not interfere with transcription of the full-length genomic RNA. In a presently preferred embodiment, the 3' UTR may be that of the ovalbumin or lysozyme genes, or any 3' UTR that is functional in a magnum cell, i.e. the SV40 late region.

In an alternative embodiment of the invention, a constitutive promoter is used to express the coding sequence of a transgene in the magnum of a bird. In this case, expression is not limited to only the magnum; expression also occurs in other tissues within the avian. However, the use of such a transgene is still suitable for effecting the expression of a protein in the oviduct and the subsequent secretion of the protein into the egg white if the protein is non-toxic to the avian in which it is expressed.

Figure 3A:
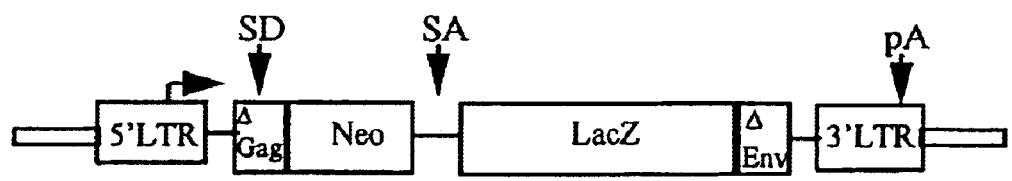
FIGS. 3(a) and 3(b) show schematic representations of the ALV-derived vectors pNLB and pNLB-CMV-BL, respectively. The vectors are both shown as they would appear while integrated into the chicken genome.
Figure 3B:
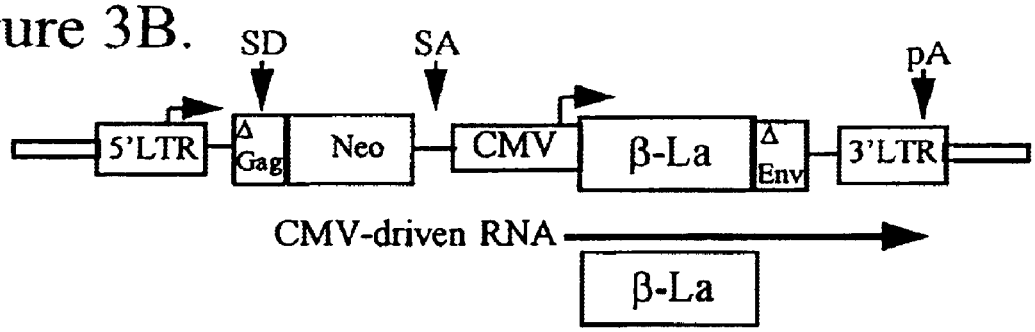

FIG. 3(a) shows a schematic of the replication-deficient avian leukosis virus (ALV)-based vector pNLB, a vector which is suitable for use in this embodiment of the invention. In the pNLB vector, most of the ALV genome is replaced by the neomycin a resistance gene (Neo) and the lacZ gene, which encodes β-galactosidase. FIG. 3(b) shows the vector pNLB-CMV-BL, in which lacZ has been replaced by the CMV promoter and the β-lactamase coding sequence (β-La or BL). Construction of the vector is reported in the specific example, Example 1, below. β-lactamase is expressed from the CMV promoter and utilizes a poly adenylation signal (pA) in the 3' long terminal repeat (LTR). β-Lactamase has a natural signal peptide; thus, it is found in blood and in egg white.

Avian embryos have been successfully transduced with pNLB-CMV-BL transduction particles (see specific examples, Example 2 and 3, below). The egg whites of eggs from the resulting stably transduced hens were found to contain up to 70 µg of secreted, active β-lactamase per egg (see specific examples, Example 4 and 5, below).

In an alternative embodiment of the invention, transgenes containing constitutive promoters are used, but the transgenes are engineered so that expression of the transgene effectively becomes magnum-specific. Thus, a method for producing an exogenous protein in an avian oviduct provided by the present invention involves generating a transgenic avian that bears two transgenes in its tubular gland cells. One transgene comprises a first coding sequence operably linked to a constitutive promoter. The second transgene comprises a second coding sequence that is operably linked to a magnum-specific promoter, where expression of the first coding sequence is either directly or indirectly dependent upon the cellular presence of the protein expressed by the second coding sequence.

Optionally, site-specific recombination systems, such as the Cre-loxP or FLP-FRT systems, are utilized to implement the magnum-specific activation of an engineered constitutive promoter. In one embodiment, the first transgene contains an FRT-bounded blocking sequence which blocks expression of the first coding sequence in the absence of FLP, and the second coding sequence encodes FLP. In another embodiment, the first transgene contains a loxP-bounded blocking sequence which blocks expression of the first coding sequence in the absence of the Cre enzyme, and the second coding sequence encodes Cre. The loxP-bounded blocking sequence may be positioned in the 5' untranslated region of the first coding sequence and the loxP-bounded sequence may optionally contain an open reading frame.

Figure 6A:
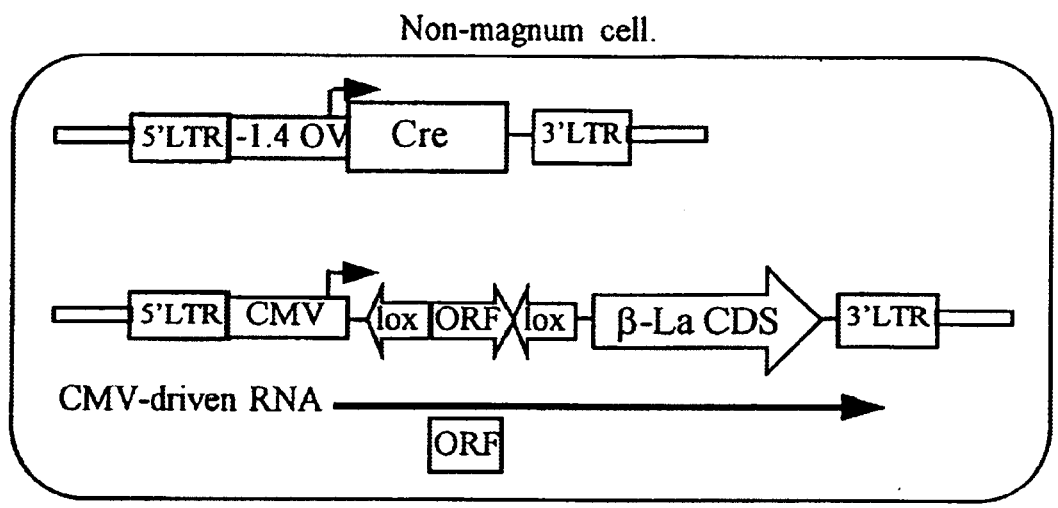
FIGS. 6(a) and 6(b) illustrate magnum-specific, recombination-activated gene expression. Schematic cre and β-lactamase transgenes are shown integrated into the genome of a hen in a non-magnum cell in FIG. 6(a).
Figure 6B:
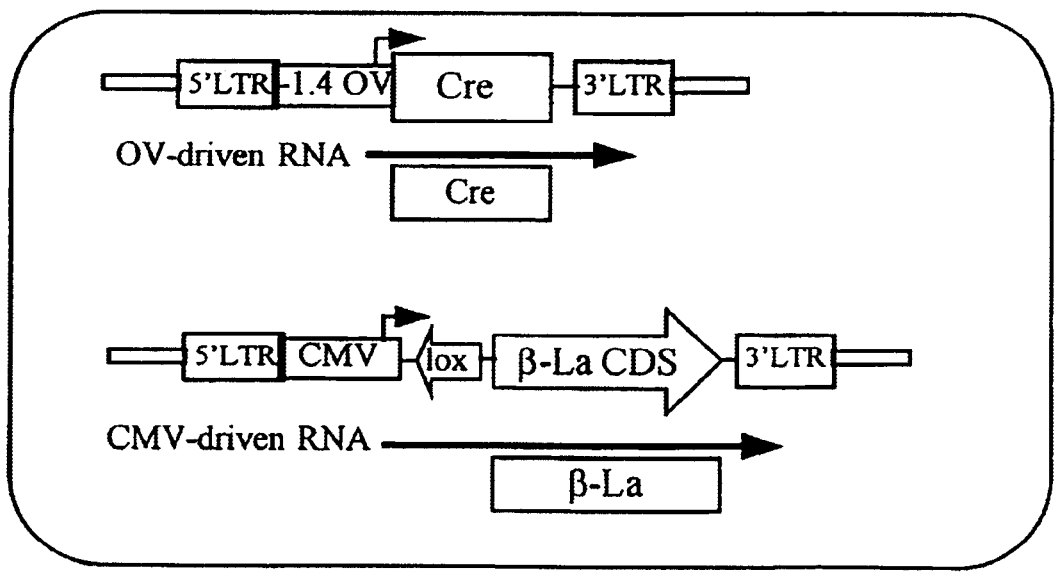

For instance, in one embodiment of the invention, magnum-specific expression is conferred on a constitutive transgene, by linking a cytomegalovirus (CMV) promoter to the coding sequence (CDS) of the protein to be secreted FIGS. 6(a) and 6(b)). The 5' untranslated region (UTR) of the coding sequence contains a loxP-bounded blocking sequence. The loxP-bounded blocking sequence contains two loxP sites, between which is a start codon (ATG) followed by a stop codon, creating a short, nonsense open reading frame (ORF). Note that the loxP sequence contains two start codons in the same orientation. Therefore, to prevent them from interfering with translation of the coding sequence after loxP excision, the loxP sites must be orientated such that the ATGs are in the opposite strand.

In the absence of Cre enzyme, the cytomegalovirus promoter drives expression of the small open reading frame (ORF) (FIG. 6(a)). Ribosomes will initiate at the first ATG, the start codon of the ORF, then terminate without being able to reinitiate translation at the start codon of the coding sequence. To be certain that the coding sequence is not translated, the first ATG is out of frame with the coding sequence's ATG. If the Cre enzyme is expressed in cells containing the CMV-cDNA transgene, the Cre enzyme will recombine the loxP sites, excising the intervening ORE (FIG. 6(b)). Now translation will begin at the start codon of the coding sequence, resulting in synthesis of the desired protein.

To make this system tissue specific, the Cre enzyme is expressed under the control of a tissue-specific promoter, such as the magnum-specific ovalbumin promoter, in the same cell as the CMV-loxP-coding sequence transgene (FIG. 6(b)). Although a truncated ovalbumin promoter may be fairly weak, it is still tissue-specific and will express sufficient amounts of the Cre enzyme to induce efficient excision of the interfering ORF. In fact, low levels of recombinase should allow higher expression of the recombinant protein since it does not compete against coding sequence transcripts for translation machinery.

Figure 7:
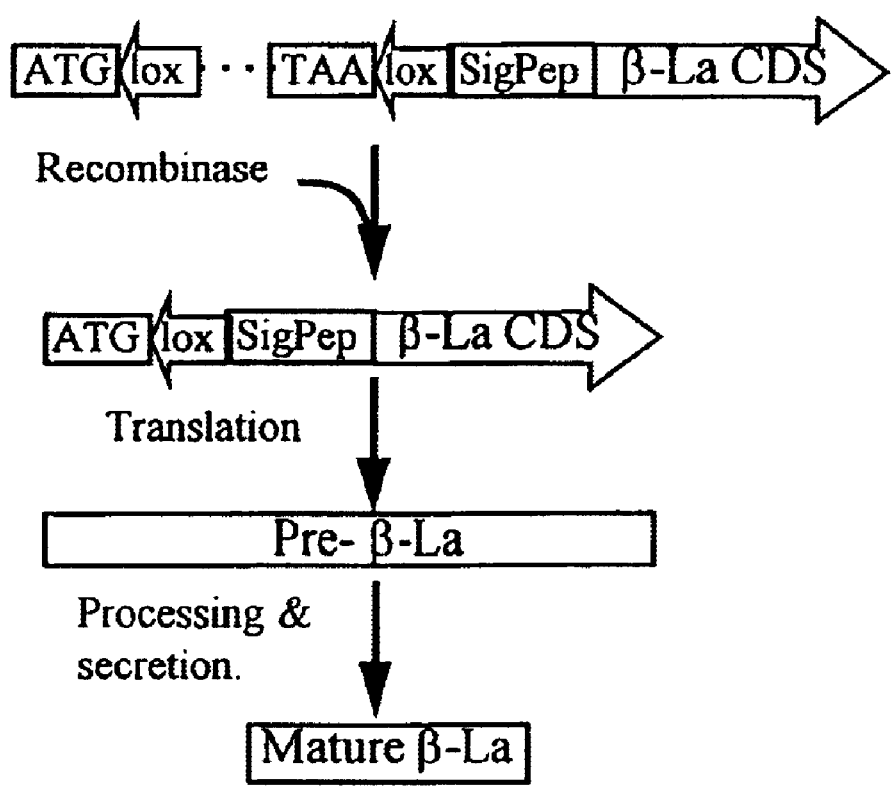
FIG. 7 illustrates an alternative method of silencing β-lactamase expression using loxP sites in which two loxP sites flanking a stop codon (TAA) in frame with the first codon (ATG) are inserted into the β-lactamase signal peptide coding sequence such that the signal peptide is not disrupted.

Alternate methods of blocking translation of the coding sequence include inserting a transcription termination signal and/or a splicing signal between the loxP sites. These can be inserted along with the blocking ORF or alone. In another embodiment of the invention, a stop codon can be inserted between the loxP sites in the signal peptide of the coding sequence (see FIG. 7). Before recombinase is expressed, the peptide terminates before the coding sequence. After recombinase is expressed (under the direction of a tissue specific promoter), the stop codon is excised, allowing translation of the coding sequence. The loxP site and coding sequence are juxtaposed such that they are in frame and the loxP stop codons are out of frame. Since signal peptides are able to accept additional sequence (Brown et al., *Mol. Gen. Genet.* 197:351–7 (1984)), insertion of loxP or other recombinase target sequences (i.e. FRT) is unlikely to interfere with secretion of the desired coding sequence. In the expression vector shown in FIG. 7, the loxP site is present in the signal peptide such that the amino acids encoded by loxP are not present in the mature, secreted protein. Before Cre enzyme is expressed, translation terminates at the stop codon, preventing expression of β-lactamase. After recombinase is expressed (only in magnum cells), the loxP sites recombine and excise the first stop codon. Therefore, β-lactamase is expressed selectively only in magnum cells.

In the aforementioned embodiments, the blocking ORF can be any peptide that is not harmful to chickens. The blocking ORF can also be a gene that is useful for production of the ALV-transduction particles and/or transgenic birds. In one embodiment, the blocking ORF is a marker gene.

For instance, the blocking ORF could be the neomycin resistance gene, which is required for production of transduction particles. Once the transgene is integrated into the chicken genome, the neomycin resistance gene is not required and can be excised.

Alternatively, β-lactamase can be used as the blocking ORF as it is an useful marker for production of transgenic birds. (For specific examples of the use of β-lactamase as a marker in transgenic birds, see Example 4, below.) As an example, the blocking ORF in FIG. 6(a) is replaced by β-lactamase and the downstream coding. sequence now encodes a secreted biopharmaceutical. β-Lactamase will be expressed in blood and other tissues; it will not be expressed in the magnum after magnum-specific expression of Cre and recombination-mediated excision of β-lactamase, allowing expression of the desired protein.

The Cre and loxP transgenes could be inserted into the chicken genome via mediated transgenesis either simultaneously or separately. Any method of transgenesis that results in stable integration into the chicken genome is suitable. Both the ovalbumin promoter-recombinase and CMV-loxP-CDS transgenes could be placed simultaneously into chickens. However, the efficiencies of transgenesis are low and therefore the efficiency of getting both transgenes into the chicken genome simultaneously is low. In an alternative and preferred method, one flock is produced that carries the magnum-specific promoter/recombinase transgene and a second is produced that carries the CMV-loxP-CDS transgene. The flocks would then be crossed to each other. Hens resulting from this outbreeding will express the coding sequence and only in their magnum.

In an alternative method of transfecting blastodermal cells to produce a transgenic chicken, a targeting vector is used for promoter-less minigene insertion (PMGI) into a target gene. The targeting vector comprises a coding sequence, at least one marker gene which is operably linked to a constitutive promoter, and targeting nucleic acid sequences which match the sequence flanking the desired point of insertion in the desired target gene. The targeting nucleic acid sequences direct insertion of the targeting vector into the target gene. The length of these targeting sequences will vary. Each targeting sequence is typically at least about 1 kb in length, although longer sequences (up to 10 kb, for instance) may be preferred in some cases and shorter sequences may be required in others. The marker gene allows for the identification of cells which have integrated the targeting vector.

In one embodiment, the target gene is an endogenous gene that is expressed in the avian oviduct. For instance, the target gene may be selected from the group consisting of ovalbumin, lysozyme, conalbumin, ovomucoid, and ovomucin. (It should be noted that because the lysozyme gene is expressed in macrophages in addition to the oviduct cells, it is not a suitable target gene when expression is desired to be restricted only to oviduct cells.)

PMGI may be used with target genes other than those expressed in the avian oviduct, and in species other than the avian species.

The point of insertion to which the vector is directed may be in either the 5' or 3' untranslated region of the target gene. If the 3' untranslated region is targeted, then the targeting vector further comprises an internal ribosome entry site element positioned directly upstream of the coding sequence on the vector.

Figure 8A:
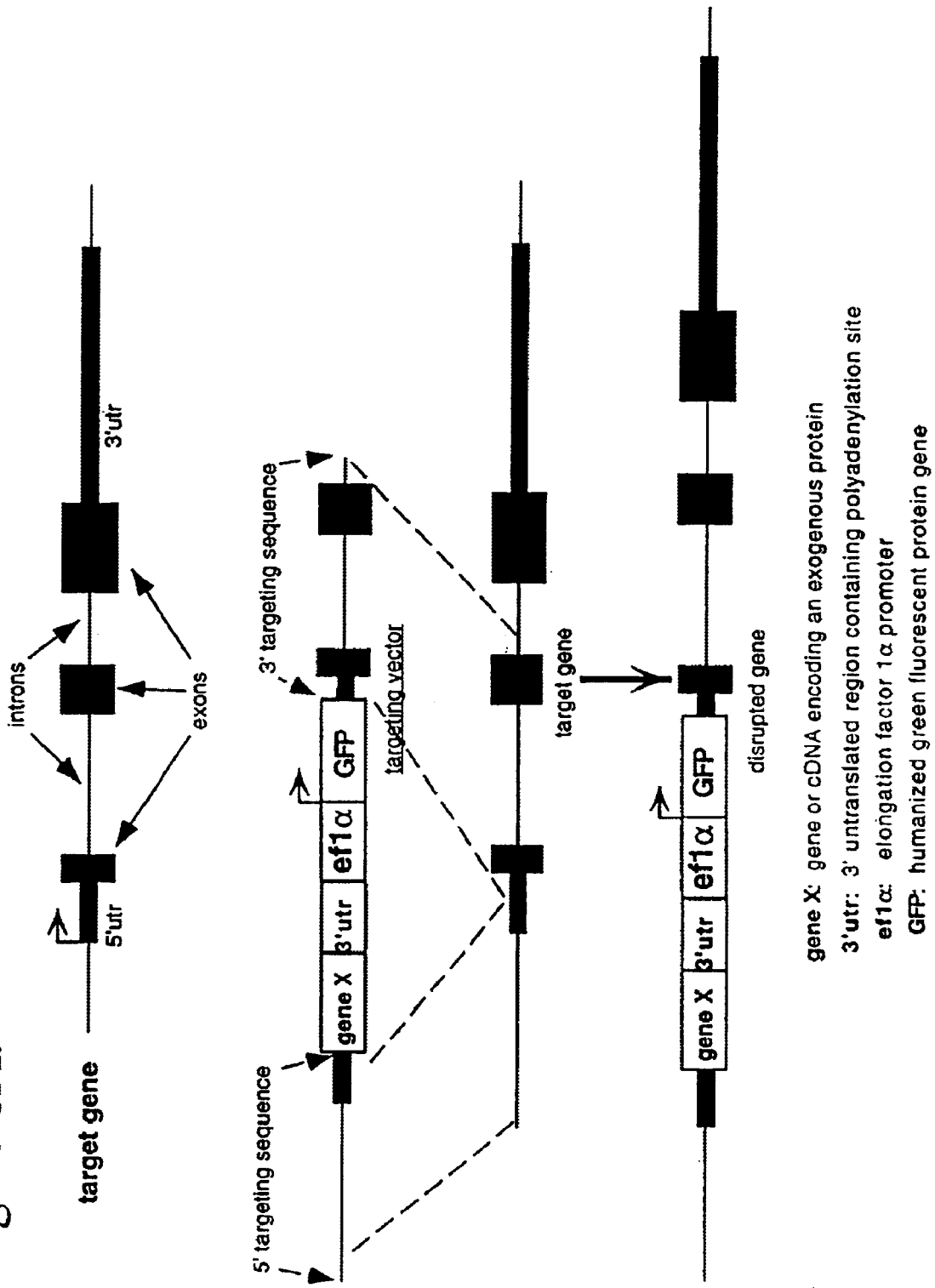
FIGS. 8(a) and 8(b) illustrate targeting vectors used for insertion of a promoter-less minigene of the invention into a target gene.
Figure 8B:
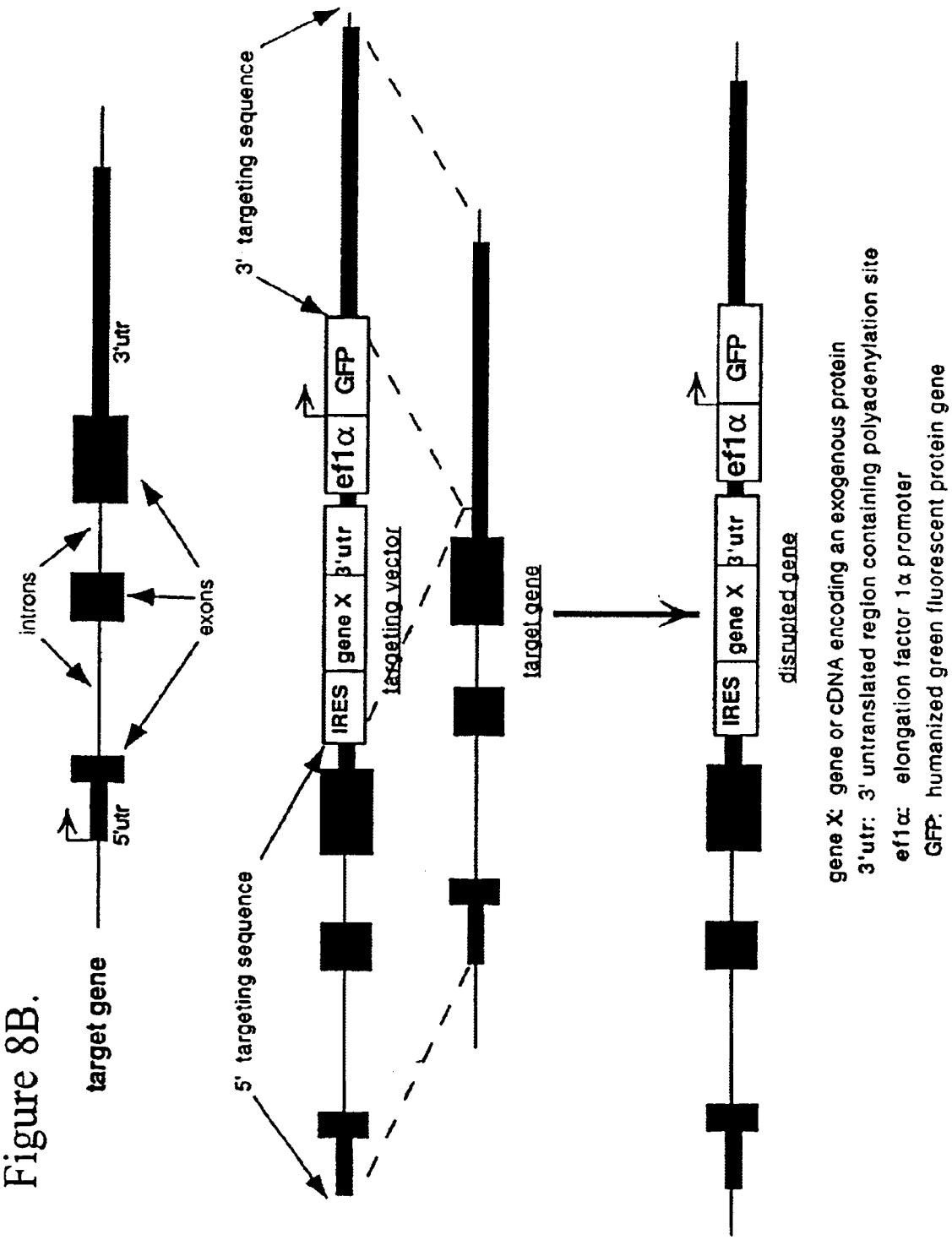

FIG. 8(a) and 8(b) illustrate the insertion of PMGI into the 5' or 3' untranslated region (UTR) of the ovalbumin target gene, respectively. In the embodiment illustrated in FIG. 8(a), a promoter-less minigene (PMG) is inserted into the 5' UTR of the ovalbumin target gene. A dicistronic mRNA encoding both the exogenous protein and ovalbumin is transcribed from the transcription start site depicted by the arrow. Ribosomes bind to the 5' end of the dicistronic mRNA, translate the exogenous gene, then terminate before translating the ovalbumin coding region. Note that the ovalbumin portion of the polycistronic transcript is not translated. Thus, the level of ovalbumin protein produced will be about half of the normal level, as translation of one copy of the ovalbumin gene is disrupted. In the embodiment illustrated in FIG. 8(b), the PMG is inserted into the 3' UTR. Translation of the exogenous gene is initiated by the presence of an IRES element to which the ribosome binds and translates the downstream coding region.

In either case, the targeting vectors contain a marker gene to enable identification and enrichment of cell clones and populations which have stably integrated the targeting vectors. Suitable identification genes include but are not limited to neo, which encodes a protein conferring resistance to G418, or GFP, which encodes the green fluorescent protein (GFP). In a preferred embodiment GFP expression is used to identify clones uniformly fluorescing green and, therefore, containing a stably integrated targeting vector. The marker gene is expressed from a ubiquitous promoter such as but not limited to the promoters of HSV tk, β-actin, CMV, or ef-1α. In a presently preferred embodiment, the ef-1α promoter drives expression of GFP.

The present invention also provides for a vector which may be used for insertion of a promoter-less minigene into a target gene, which comprises the elements of the targeting vector described above but also includes a second marker gene which is operably linked to a second constitutive promoter. The second marker gene is positioned outside the targeting nucleic acid sequences of the targeting vector, so that upon insertion of the promoter-less minigene into the target gene, the second marker gene will not be inserted.

Figure 9:
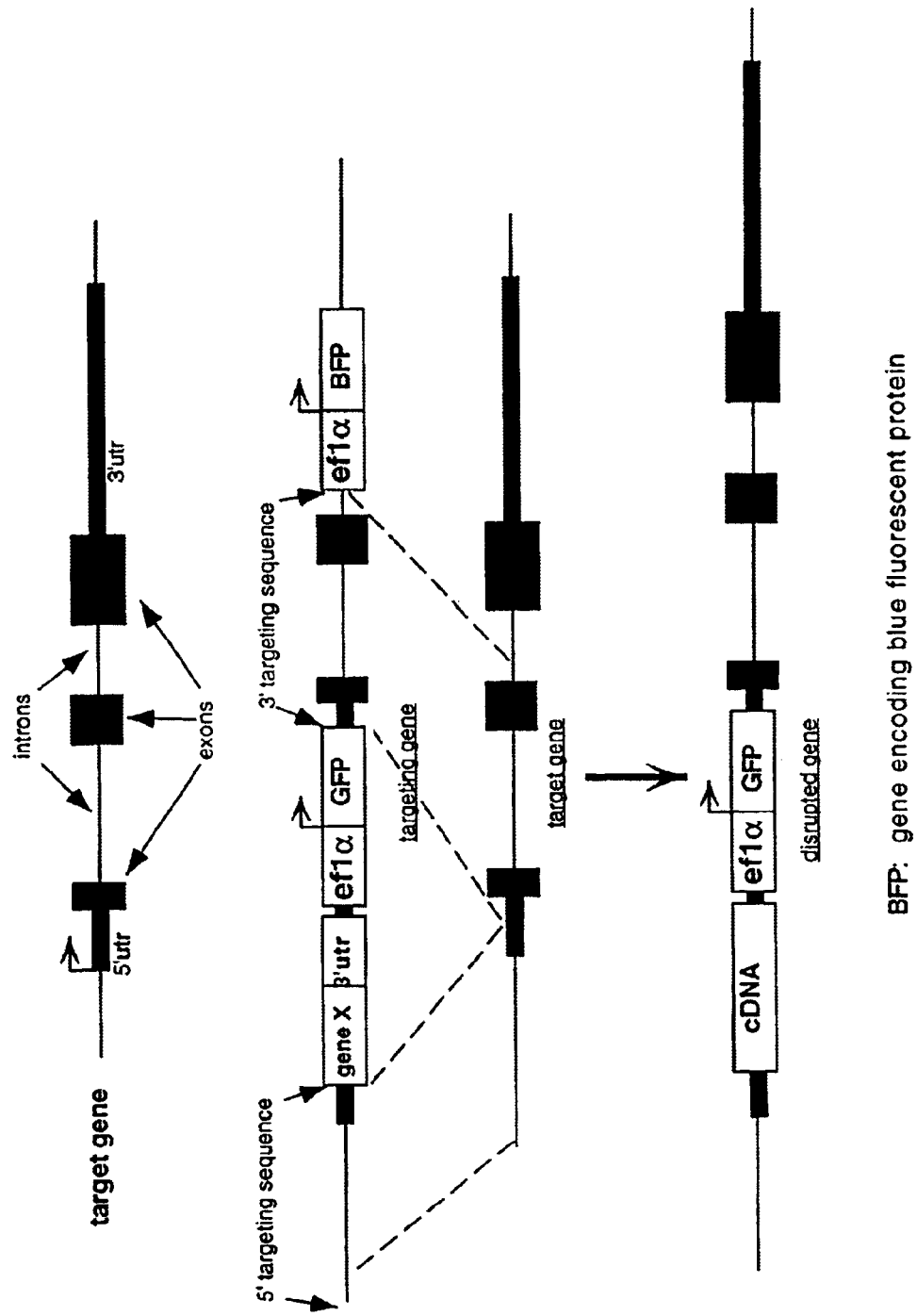
FIG. 9 illustrates a targeting vector used for detecting correct homologous insertion of a promoter-less minigene of the invention into a target gene.

For instance, one embodiment of the invention involves use of marker genes encoding blue fluorescent protein (BFP) and GFP in the PMGI targeting vector (FIG. 9). This strategy is a variation of the positive-negative selection strategy (U.S. Pat. Nos. 5,464,764 and 5,487,992 (Capecchi et al.), in which BFP is used to identify the rare cells in which the promoter-less minigene (PMG) has correctly inserted into the target gene. The BFP gene is inserted on the 3' end of the original targeting vector (See FIG. 9). When the targeting vector and target correctly undergo homologous recombination, only the GFP gene is inserted. Thus, colonies containing a correctly inserted PMG will fluoresce green. By contrast, in the majority of cells, the entire vector, including the BFP gene, will insert at random spots in the genome. Colonies in which random insertion has taken place will fluoresce blue and green due to the presence of GFP and BFP.

Although FIG. 9 illustrates use of this vector in the 5' UTR, this vector is suitable for use in either the 5' or 3' UTR.

As mentioned above, the vectors produced according to the methods of the invention may optionally be provided with a 3' UTR containing a polyadenylation site to confer stability to the RNA produced. In a preferred embodiment, the 3' UTR may be that of the exogenous gene, or selected from the group consisting of the ovalbumin, lysozyme, or SV40 late region However, the ovalbumin 3' UTR is not suitable in a PMGI vector that is to be inserted into the endogenous ovalbumin gene because the addition of ovalbumin sequences to the PMGI vector will interfere with proper targeting.

c) Production of Exogenous Protein

Methods of the invention which provide for the production of exogenous protein in the avian oviduct and the production of eggs which contain exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced in the previous steps. Deriving a mature transgenic avian from the blastodermal cells optionally involves transferring the transgenic blastodermal cells to an embryo and allowing that embryo to develop fully, so that the cells become incorporated into the bird as the embryo is allowed to develop. The resulting chick is then grown to maturity. In alternative embodiment, the cells of a blastodermal embryo are transfected or transduced with the vector directly within the embryo. The resulting embryo is allowed to develop and the chick allowed to mature.

In either case, the transgenic bird so produced from the transgenic blastodermal cells is known as a founder. Some founders will carry the transgene in the tubular gland cells in the magnum of their oviducts. These birds will express the exogenous protein encoded by the transgene in their oviducts. If the exogenous protein contains the appropriate signal sequences, it will be secreted into the lumen of the oviduct and onto the yolk of an eggs.

Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic bird will have tubular gland cells expressing the exogenous protein and the offspring of the transgenic bird will also have oviduct magnum tubular gland cells that express the exogenous protein. (Alternatively, the offspring express a phenotype determined by expression of the the exogenous gene in a specific tissue of the avian.)

The invention can be used to express, in large yields and at low cost, a wide range of desired proteins including those used as human and animal pharmaceuticals, diagnostics, and livestock feed additives. Proteins such as human growth hormone, interferon, lysozyme, and β-casein are examples of proteins which are desirably expressed in the oviduct and deposited in eggs according to the invention. Other possible proteins to be produced include, but are not limited to, albumin, 60 -1 antitrypsin, antithrombin III, collagen, factors VIII, IX, X (and the like), fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin. Genetically engineered antibodies, such as immunotoxins which bind to surface antigens on human tumor cells and destroy them, can also be expressed for use as pharmaceuticals or diagnostics.

d) EXAMPLES

The following specific examples are intended to illustrate the invention and should not be construed as limiting the scope of the claims.

Example 1

Vector Construction

The lacZ gene of pNLB, a replication-deficient avian leukosis virus (ALV)-based vector (Cosset et al., 1991), was replaced with an expression cassette consisting of a cytomegalovirus (CMV) promoter and the reporter gene, β-lactamase (β-La or BL). The pNLB and pNLB-CMV-BL vector constructs are diagrammed in FIGS. 3(a) and 3(b), respectively.

To efficiently replace the lacZ gene of pNLB with a transgene, an intermediate adaptor plasmid was first created, pNLB-Adapter. pNLB-Adapter was created by inserting the chewed back ApaI/ApaI fragment of pNLB (Cosset et al., *J Virol.* 65:3388–94 (1991)) (in pNLB, the 5' ApaI resides 289 bp upstream of lacZ and the 3' ApaI resides 3' of the. 3' LTR and Gag segments) into the chewed-back KpnI/SacI sites of pBluescriptKS(-). The filled-in MluI/XbaI fragment of pCMV-BL (Moore et al., *Anal. Biochem.* 247: 203–9 (1997)) was inserted into the chewed-back KpnI/NdeI sites of pNLB-Adapter, replacing lacZ with the CMV promoter and the BL gene (in pNLB, KpnI resides 67 bp upstream of lacZ and NdeI resides 100 bp upstream of the lacZ stop codon), thereby creating pNLB-Adapter-CMV-BL. To create pNLB-CMV-BL, the HindIII/BlpI insert of pNLB (containing lacZ) was replaced with the HindIII/BlpI insert of pNLB-Adapter-CMV-BL. This two step cloning was necessary because direct ligation of blunt-ended fragments into the HindIII/BlpI sites of pNLB yielded mostly rearranged subclones, for unknown reasons.

Example 2

Production of Transduction Particles

Sentas and Isoldes were cultured in FIO (Gibco), 5% newborn calf serum (Gibco), 1% chicken serum (Gibco), 50 µg/ml phleomycin (Cayla Laboratories) and 50 µg/ml hygromycin (Sigma). Transduction particles were produced as described in Cosset et al., 1993, herein incorporated by reference, with the following exceptions. Two days after transfection of the retroviral vector pNLB-CMV-BL (from Example 1, above) into $9 \times 10^5$ Sentas, virus was harvested in fresh media for 6–16 hours and filtered. All of the media was used to transduce $3 \times 10^6$ Isoldes in 3 100 mm plates with polybrene added to a final concentration of 4 µg/ml. The following day the media was replaced with media containing 50 µg/ml phleomycin, 50 µg/ml hygromycin and 200 µg/ml G4 18 (Sigma).

After 10–12 days, single G418' colonies were isolated and transferred to 24-well plates. After 7–10 days, titers from each colony was determined by transduction of Sentas followed by G418 selection. Typically 2 out of 60 colonies gave titers at $1-3 \times 10^5$. Those colonies were expanded and virus concentrated to $2-7 \times 10^7$ as described in Allioli et al., *Dev. Biol.* 165:30–7 (1994), herein incorporated by reference. The integrity of the CMV-BL expression cassette was confirmed by assaying for β-lactamase in the media of cells transduced with NLB-CMV-BL transduction particles.

Example 3

Production of Transgenic Chickens

Stage X embryos in freshly laid eggs were transduced with NLB-CMV-BL transduction particles (from Example 2, above) as described in Thoraval et al., *Transgenic Res.* 4:369–377 (1995), herein incorporated by reference, except that the eggshell hole was covered with 1–2 layers of eggshell membrane and, once dry, Duco model cement.

Approximately 120 White Leghorns were produced by transduction of the stage X embryos with NLB-CMV-BL transduction particles. These birds constitute chimeric founders, not fully transgenic birds. Extensive analysis of DNA in the blood and sperm from the transduced chickens indicates that 10–20% of the birds had detectable levels of the transgene in any given tissue. Of those birds carrying the transgene, approximately 0–1.0% of the cells in any given tissue were actually transgenic.

Example 4

β-lactamase Activity Assay in Blood and Egg White

When hens produced in Example 3, above, began to lay eggs, the egg whites of those eggs were assayed for the presence of β-lactamase. The β-lactamase assay was carried out as described in Moore et al., *Anal. Biochem.* 247:203–9 (1997), herein incorporated by reference, with the following modifications.

To assay blood from two to ten day old chicks, the leg vein was pricked with a scalpel. 50 µl of blood was collected in a heparinized capillary tube (Fisher), of which 25 µl was transferred to 100 µl phosphate-buffered saline (PBS) in a 96-well plate. Various dilutions of purified β-lactamase (Calbiochem) was added to some wells prior to addition of blood from control (non-transduced) chicks to establish a β-lactamase standard curve. After one day at 4° C., the plate was centrifuged for 10 minutes at 730×g. 25 µl of the supernatant was added to 75 µl of PBS. 100 µl of 20 µM 7-(thienyl-2-acetamido)-3-[2-(4-N,N-dimethylamnino-phenylazo)pyridinium-methyl]-3-cephem-4-carboxylic acid (PADAC, from Calbiochem) in PBS was added, and the wells were read immediately on a plate reader in a 10 minute kinetic read at 560 nm or left overnight in the dark at room temperature. Wells were scored positive if the well had turned from purple to yellow. To assay blood from older birds, the same procedure was followed except that 200–300 µl blood was drawn from the wing vein using a syringe primed with 50 µl of heparin (Sigma).

Analysis of the NLB-CMV-BL transduced flock revealed nine chickens that had significant levels of β-lactamase in their blood. Three of these chickens were males and these were the only three males that had significant levels of the NLB-CMV-BL transgene in their sperm as determined by PCR analysis (see Example 10, below). Thus, these are the males that are to be outbred to obtain fully transgenic $G_1$ offspring. The other six chickens were the hens that expressed β-lactamase in their magnum tissue (see below). Other birds had low levels of β-lactamase (just above the level of detection) in their blood but did not have transgenic sperm or eggs containing β-lactamase. Thus β-lactamase expression in blood is a strong indicator of whether a chicken was successfully transduced.

To assay β-lactamase in egg white, freshly laid eggs were transferred that day to a 4° C. cooler, at which point the β-lactamase is stable for at least one month. (Bacterially-expressed, purified β-lactamase added to egg white was determined to lose minimal activity over several week at 4° C., confirming the stability of β-lactamase in egg white.) To collect egg white samples, eggs were cracked onto plastic wrap. The egg white was pipetted up and down several times to mix the thick and thin egg whites. A sample of the egg white was transferred to a 96 well plate. 10 µl of the egg white sample was transferred to a 96-well plate containing 100 µl of PBS supplemented with 1.5 µl of 1 M $NaH_2PO_4$, pH 5.5 per well. After addition of 100 µl of 20 µM PADAC, the wells were read immediately on a plate reader in a 10 minute or 12 hour kinetic read at 560 nm. Various dilutions of purified β-lactamase was added to some wells along with 10 µl of egg white from control (non-transduced) hens to establish a β-lactamase standard curve. Egg white from both untreated and NLB-CMV-BL transduced hens were assayed for the presence of β-lactamase.

Figure 4:
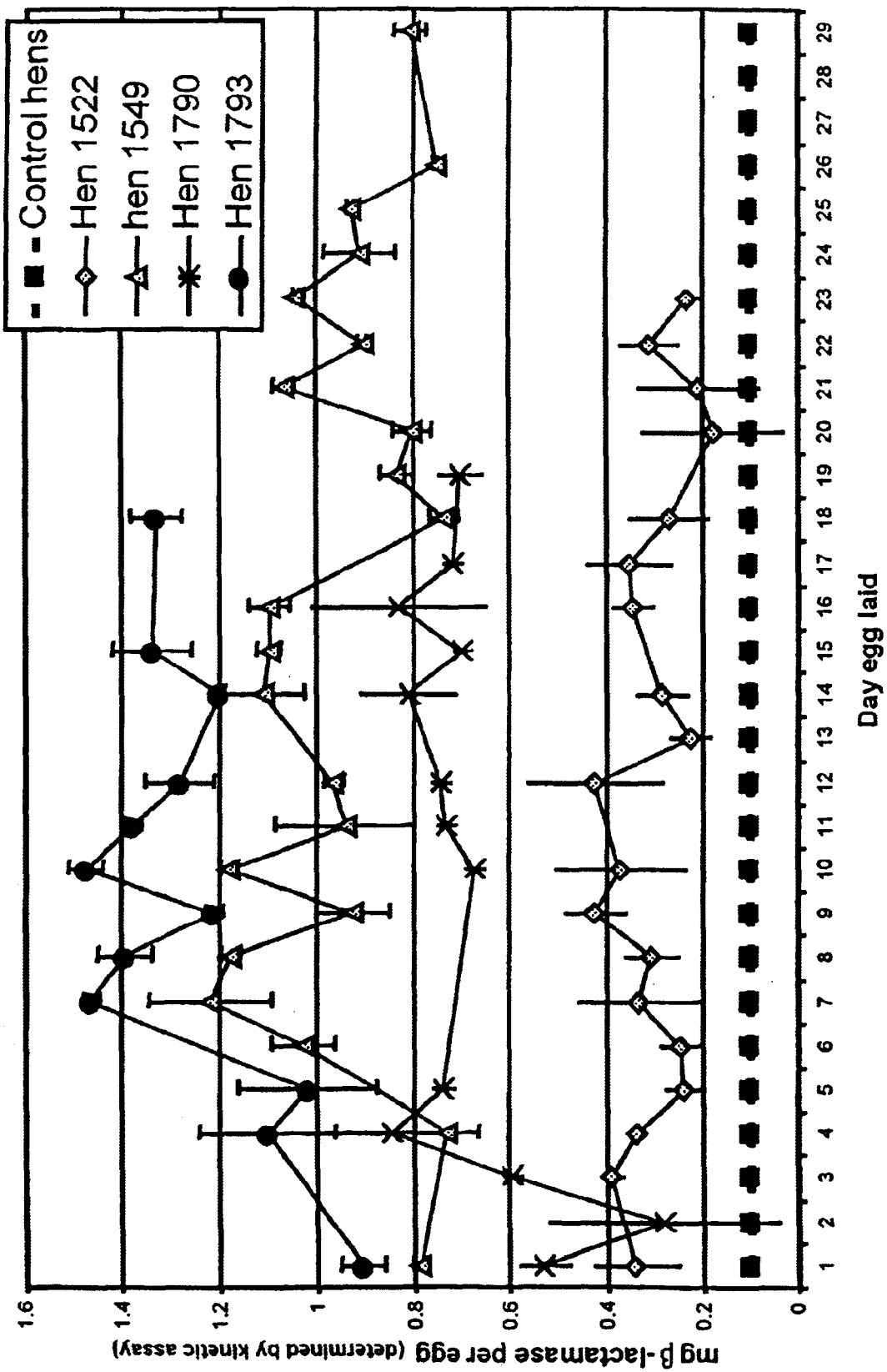
FIG. 4 shows a graph showing the amount of β-lactamase found in the egg white of eggs from hens transduced with NLB-CMV-BL, as determined by the β-lactamase activity assay.

Significant levels of β-lactamase were detected in the egg white of six hens, as shown in FIG. 4 and Table 1, below. Eggs laid by Hen 1522 ("Betty Lu"), the first hen to demonstrate expression in eggs, Typically have 70 µg or higher of active β-lactamase per egg. Also shown is β-lactamase production from three other NLB-CMV-BL transduced hens (Hen 1549, Hen 1790 and Hen 1593). Every hen that laid eggs containing β-lactamase also had significant levels of β-lactamase in its blood.

TABLE 1

Expression of β-lactamase in eggs of NLB-CMV-BL treated hens.

| | Hen # | Average µg of β-lactamase per egg | # of eggs assayed |
|---|---|---|---|
| 1. | Control | −0.49 ± 1.73 | 68 |
| 2. | 1522 | 9.9 ± 3.1 | 59 |
| 3. | 1549 | 33.5 ± 7.0 | 61 |
| 4. | 1581 | 69.2 ± 14.9 | 51 |
| 5. | 1587 | 62.6 ± 5.8 | 54 |
| 6. | 1790 | 29.0 ± 2.4 | 52 |
| 7. | 1793 | 49.9 ± 6.2 | 51 |

Control eggs are eggs from untreated hens. The low level of BL in these eggs is due to spontaneous breakdown of PADAC during the course of the kinetic assay. The other hens were transduced with NLB-CMV-BL as described in Example 3. Egg white from each egg was assayed in triplicate.

Based on the β-lactamase activity assay, the expression levels of β-lactamase appeared to range from 10 to 70 µg per egg (assuming 40 milliliters of egg white per egg).

Example 5

Western Blot of β-Lactamase in Egg White

Western blot analysis of the same egg white as was assayed in Example 4 confirmed the presence of β-lactamase and provided another measurement of the amount of β-lactamase present in the egg than the kinetic assay of Example 4, above.

To perform the analysis, 10 µl of egg white was added to 30 µl of 0.5 M Tris-Cl, pH 6.8, 10% sodium dodecyl sulfate (SDS), 10% glycerol, 1.43 M 2-mercaptoethanol, 0.001% bromophenol blue. Samples were heated to 95° C. for 5 min, separated on 12% SDS-PAGE and transferred to Immobilon P membranes (Millipore). β-lactamase was detected with 1:500 dilution of rabbit anti-β-lactamase (5 Prime-3 Prime) and 1:5000 dilution of goat anti-rabbit IgG HRP conjugate (Promega). Immunoblots were visualized with the Enhanced Chemiluminescence (ECL) Western Blotting System (Amersham).

Figure 5:
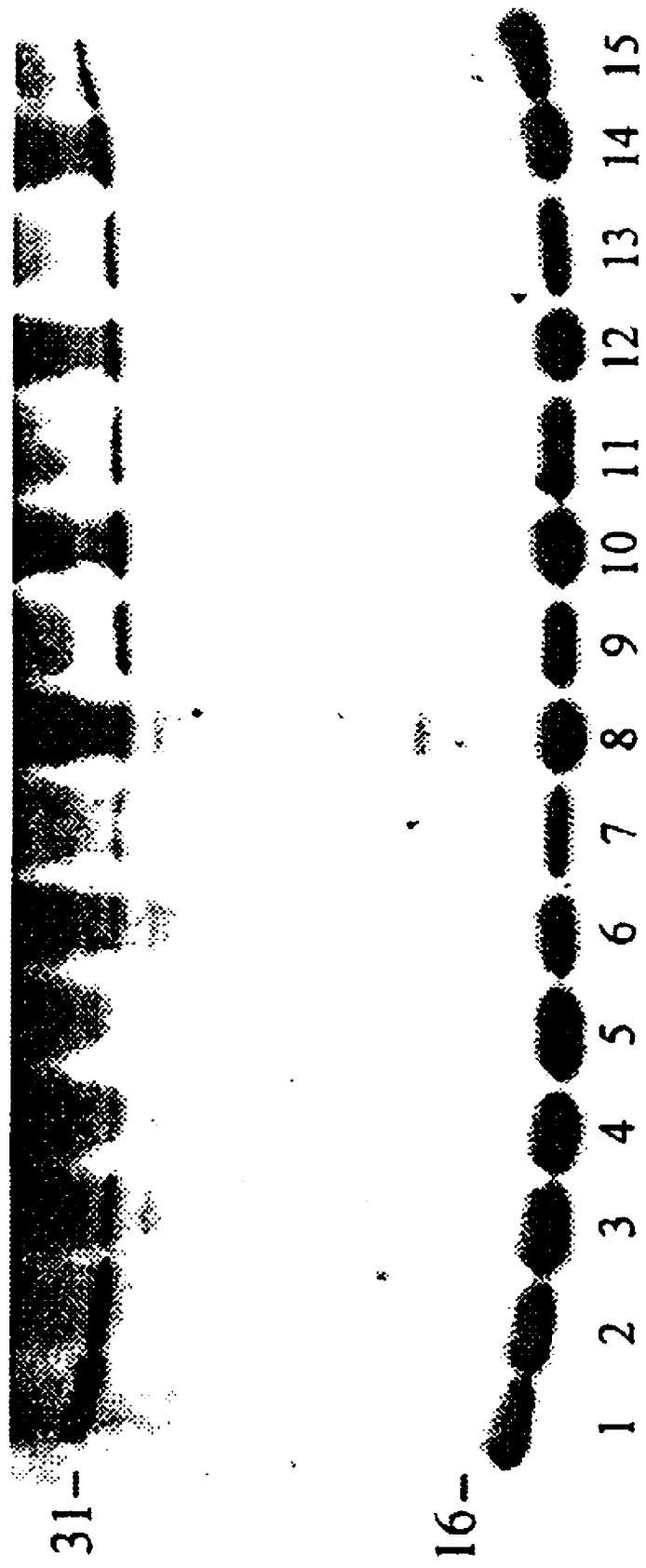
FIG. 5 shows a western blot indicating the presence of β-lactamase in the egg white of eggs from hens transduced with NLB-CMV-BL.

Various β-lactamase samples were analyzed by western blotting and anti-β-lactamase antibody. The results are shown in FIG. 5. Lanes 1–4 of the blot contain 236, 59, 15, and 3.6 ng, respectively, of bacterially expressed, purified β-lactamase added to control egg white, forming a standard curve. Lane 5 contains control egg white from an untreated hen. In lane 6 is 2 µl of egg white from Hen 1522 (Betty Lu). Lanes 7–8 contain 1 and 2 µls, respectively, of egg white from Hen 1790. Lanes 9–10 contain 1 and 2 µls, respectively, of egg white from Hen 1793. 1 and 2 µls aliquots of egg white from Hen 1549 was run in lanes 11–12. Lanes 13–14 show 1 and 2 µls, respectively, of egg white from Hen 1581. 2 µls of egg white from Hen 1587 is shown in lane 15.

The position of molecular weight standards is noted in FIG. 5 to the left of the blot in kilodaltons (kDa). The band at 31 kDa is β-lactamase. The molecular weight of the β-lactamase in the egg white is similar to that of purified β-lactamase. The egg white 62-lactamase is also a single molecular species, indicating that synthesis was faithful to the 62-lactamase coding sequence and that β-lactamase is very stable in magnum cells as well as egg white. The band at 13 kDa is an egg white protein that cross-reacts with the anti-β-lactamase antibody.

Based on the western blot results, β-lactamase in lane 6 (from Hen 1522, Betty Lu) is estimated at 5 ng or 100 µg per egg, assuming 40 mls of egg white per egg. β-Lactamase in lane 9 (from Hen 1793) is estimated at 15 ng which corresponds to 600 µg per egg. The β-lactamase levels per egg as estimated by the western blot analysis were considerably higher (up to 10-fold higher) than the levels estimated by the β-lactamase enzyme assay of Example 4.

It should be noted that the amount of β-lactamase per egg reported here (up to 600 µg) was produced by chimeric founders, not fully transgenic birds. As reported above, only 0.1–1% of the cells in any given tissue of the chimeric founders were actually transgenic. Assuming that this extent of mosaicism also applies to magnum tissue, then the magnums of the six β-lactamase egg-positive hens were only partially transgenic. Therefore, fully transgenic birds ($G_1$ offspring) would be expected to express much higher levels, possibly as high as 20–40 mg/egg. This estimate is significant because it indicates that non-magnum specific promoters such as CMV can effectively compete with magnum specific genes such as ovalbumin and lysozyme for the egg-white protein synthesis machinery.

Example 6

Isolation and Ex Vivo Transfection of Blastodermal Cells

In an alternative embodiment of the invention, blastodermal cells are transfected ex vivo with an expression vector.

In this method, donor blastodermal cells are isolated from fertilized eggs of Barred Plymouth Rock hens using a sterile annular ring of Whatman filter paper which is placed over a blastoderm and lifted after cutting through the yolk membrane of the ring. The ring bearing the attached blastoderm is transferred to phosphate-buffered saline (PBS) in a petri dish ventral side up, and adhering yolk is removed by gentle pipetting. The area opaca is dissected away with a hair loop and the translucent stage X blastoderm is transferred via a large-bore pipette tip to a microfuge tube. About 30,000–40,000 cells are isolated per blastoderm and for a typical experiment 10 blastoderms are collected.

Cells are dispersed by brief trypsin (0.2%) digestion, washed once by low speed centrifigation in Dulbecco's modified Eagle's medium (DMEM) and then transfected with linearized plasmids via lipofectin (16 µg/200 µl, BRL) for 3 hours at room temperature. The vectors shown in FIGS. 1, 3, or 4 would serve as suitable expression constructs here. Cells are washed free of lipofectin with medium and then 400–600 cells are injected a into y-irradiated (650 rads) recipient stage X embryos from the Athens-Canadian randombred line (AC line). Injection is through a small window (~0.5 cm) into the subgerminal cavity beneath the recipient blastoderms. Windows are sealed with fresh egg shell membrane and Duco plastic cement. Eggs are then incubated at 39.1° C. in a humidified incubator with 90° rotation every 2 hr.

Example 7

Identification of Transgenic Mosaics by PCR Assay

Among the chicks which hatch from embryos containing transfected or transduced blastodermal cells, only those exhibiting Barred Plymouth Rock feather mosaicism are retained. Even if no reporter gene is present in the transgene, transgenic mosaics can be identified by PCR assay.

To identify transgenic mosaics, DNA blood and black feather pulp of individual chicks are assayed by PCR for the presence of the transgene using a primer pair specific to the transgene as described by Love et al., *Bio/Technology* 12:60–63 (1994). Transgene chimeras are induced, withdrawn and re-induced with diethylstilbestrol (DES) pellets and excised magnums analyzed for expression of reporter activity. Blood and liver are assayed to monitor tissue specificity.

Male and female blood DNA was collected at 10 to 20 days post-hatch. The DNA is extracted from the blood using a novel high-throughput method of DNA extraction developed in our laboratory. In this method, blood is drawn from a wing vein into a heparinized syringe and one drop is immediately dispensed into one well of a flat-bottom 96-well dish containing a buffer which lyses cytoplasmic membranes exclusively. The plate is then briefly centrifuged, which pellets the nuclei. The supernatant is removed and a second lysis buffer is added which releases genomic DNA from nuclei and degrades nucleases. The DNA is ethanol precipitated in the plate, washed with 70% ethanol, dried and resuspended in 100 µl of water per well. As much as 80 µg of DNA can be obtained from one drop (8 µl) of chick blood. At least 768 samples can be processed by one person in one day and the DNA is suitable for PCR and Taqman™ (Perkin Elmer/Applied Biosystems) analysis.

The isolated DNA is then tested for the presence of the transgenes using the Taqman sequence detection assay to evaluate the efficiency of the embryo transduction process. The Taqman sequence detection system allows the direct detection of a specific sequence. A fluorescently-labeled oligonucleotide probe complementary to an internal region of a desired PCR product only fluoresces when annealed to the desired PCR product, which in this case is complementary to the transgene. Because all of the detection occurs in the PCR tube during the cycling process, the Taqman system allows high-throughput PCR (no gel electrophoresis is need) as well as sequence detection analogous to and as sensitive as Southern analysis. 1 µl of the isolated DNA, which contains 600–800 ng of DNA, is used for the Taqman reaction. Each reaction contains two sets of primer pairs and Taqman probes. The first set detects the chicken glyceraldehyde 3-phosphate dehydrogenase gene (GAPDH) and is used as an internal control for the quality of the genomic DNA and also serves as a standard for quantitation of the transgene dosage. The second set is specific for the desired transgene. The two Taqman probes are attached to different dyes which fluoresce at unique wavelengths: thus both PCR products are detected simultaneously in an ABI/PE 7700 Sequence Detector. It is estimated that up to 180 birds will hatch, and 20% (36 birds) will contain the transgene in their blood.

Example 8

Identification of Blastodermal Cells with a Correctly Integrated Promoter-Less Minigene (PMG)

Following transfection with a PMGI targeting vector such as those shown in FIG. 8, cells are grown on a feeder line in conditioned medium to produce colonies in which all or nearly half of the cells are uniformly green in fluorescence. Fluorescence is detected in a dissecting stereomicroscope equipped with epifluorescence detection. Uniform fluorescence indicates that the vector has stably integrated into the genome. Of these cell clones, only a small subset actually have the PMG inserted correctly in the target gene. The majority of the clones have PMG integrated randomly into the genome. To identify clones containing a correctly integrated PMG, colonies are screened using a TaqMan PCR assay, as described above. Two primers are used to amplify a segment of the transgene at its site of integration. One primer lies in gene X, the exogenous gene to be expressed in the oviduct, and the other just outside the 5' targeting sequence, so that the fragment can only be amplified by correct insertion into the target gene. Colonies containing a correctly integrated transgene are subjected to limited passage in culture on feeder cells in the presence of a variety of cytokines that promote their growth in the absence of differentiation. Cells are injected into recipient embryos. Alternatively, green colonies are pooled and injected into recipient embryos. Hatched chicks are screened subsequently for the presence of the correctly inserted transgene.

Example 9

Blue/Green Detection for Promoter-Less Minigene Insertion (PMGI)

Following transfection with a PMGI targeting vector like that of FIG. 9, cells are grown for one day in the absence of a feeder layer and green cells separated from blue/green cells using a fluorescence-activated cell sorter the next day. Green cells are then briefly passaged on feeder cells prior to injection into recipient embryos. Green cells are also screened as above for correct insertion.

Example 10

Production of Fully Transgenic $G_1$ Chickens

Males are selected for breeding because a single male can give rise to 20 to 30 $G_1$ offspring per week as opposed to 6 $G_1$ offspring per female per week, thereby speeding the expansion of $G_1$ transgenics. The feed of $G_0$ males is supplemented with sulfamethazine, which accelerates the sexual maturation of males such that they can start producing sperm at 10–12 weeks of age instead of 20–22 weeks without influencing their health or fertility (Speksnijder and Ivarie, unpublished data).

Sperm DNA of all males are screened for the presence of the transgene. Sperm are collected and the DNA extracted using Chelex-100. Briefly, 3 µl of sperm and 200 µl of 5% Chelex-100 are mixed, followed by addition of 2 µl of 10 mg/ml proteinase K and 7 µl of 2 M DTT. Samples are incubated at 56° C. for 30–60 minutes. Samples are boiled for 8 minutes and vortexed vigorously for 10 seconds. After centrifugation at 10 to 15 kG for 2–3 minutes, the supernatant is ready for PCR or Taqman analysis. The DNAs are analyzed by the Taqman assay using a Taqman probe and primers complementary to the transgene. Of the 90 $G_0$ males, it is estimated that 5%, or 4 to 5, will have the transgene in their sperm DNA.

As noted above in Example 4, the NLB-CMV-BL transduced flock included three males that had significant levels of the NLB-CMV-BL transgene in their sperm as determined by PCR analysis (see Example 10). Thus, these males are chosen for further breeding to obtain fully transgenic $G_1$ offspring.

By breeding germline transgenic males to 90 non-transgenic White Leghorn females per week, it is estimated that 16 $G_1$ offspring per week will be obtained. Hatched chicks are vent-sexed and screened for the presence of the transgene in their blood DNA by the Taqman assay. Twenty male and female $G_1$ transgenics will be obtained or 40 total, which will take up to 3 weeks.

Males will be kept for further breeding and females tested for expression of transgenes in the egg.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method for producing an exogenous interferon α or erythropoietin protein in an egg of a chicken, which method comprises:
   a) providing an avian leukosis viral vector comprising a nucleic acid sequence encoding an exogenous interferon a or erythropoietin protein, and a constitutive promoter operably linked to said sequence, wherein said promoter drives expression of the encoding sequence in the chicken oviduct;
   b) introducing said vector into chicken stage X embryonic cells;
   c) incubating said embryonic cells under conditions conducive to hatching live chicks;
   d) nurturing growth of a mature chimeric chicken from said chicks;
   e) mating said chimeric chicken, either naturally or via artificial insemination, with a non-transgenic chicken;
   f) identifying a transgenic chicken by screening the progeny of step e) for germ line incorporation of the protein encoding sequence; and
   g) mating the transgenic progeny with non-transgenic chickens to produce eggs containing the exogenous protein.

2. A method of claim 1 for producing an exogenous interferon α protein.

3. A method of claim 1 for producing an exogenous erythropoietin protein.

4. The method of claim 1 further comprising extracting the exogenous protein from the egg.

5. A method for producing an exogenous interferon α or erythropoietin protein in an egg of a chicken, which method comprises:
   a) providing an avian leukosis viral vector comprising a nucleic acid sequence encoding an exogenous interferon α or erythropoietin protein, and a constitutive promoter operably linked to said sequence, wherein said promoter drives expression of the encoding sequence in the chicken oviduct;
   b) introducing said vector into chicken stage X embryonic cells;
   c) incubating said embryonic cells under conditions conducive to hatching live chicks;
   d) nurturing growth of a mature chimeric chicken from said chicks;
   e) mating said chimeric chicken, either naturally or via artificial insemination, with a non-transgenic chicken;
   f) identifying a transgenic chicken by screening the progeny of step e) for germ line incorporation of the protein encoding sequence;
   g) mating the transgenic progeny with non-transgenic chickens to produce said egg containing the exogenous protein; and
   h) extracting the exogenous protein from the egg.

6. A method of claim 5 for producing an exogenous interferon α protein.

7. A method of claim 5 for producing an exogenous erythropoietin protein.

* * * * *

UNITED STATES PATENT AND TRADEMARK OFFICE
CERTIFICATE OF CORRECTION

PATENT NO. : 6,730,822 B1  
APPLICATION NO. : 09/173864  
DATED : May 4, 2004  
INVENTOR(S) : Ivarie et al.

Page 1 of 1

It is certified that error appears in the above-identified patent and that said Letters Patent is hereby corrected as shown below:

On the Title Page, Item (54) Title:

change "VECTORS IN AVIAN TRANSGENESIS" to --METHODS FOR PRODUCING INTERFERON AND ERYTHROPOIETIN--

On the Title Page, Item (73) Assignee:

add --University of Georgia Research Foundation, Inc., Athens, GA (US)--

Signed and Sealed this

Fourth Day of December, 2007

JON W. DUDAS  
*Director of the United States Patent and Trademark Office*

UNITED STATES PATENT AND TRADEMARK OFFICE
CERTIFICATE OF CORRECTION

| | | |
|---|---|---|
| PATENT NO. | : 6,730,822 B1 | Page 1 of 1 |
| APPLICATION NO. | : 09/173864 | |
| DATED | : May 4, 2004 | |
| INVENTOR(S) | : Ivarie et al. | |

It is certified that error appears in the above-identified patent and that said Letters Patent is hereby corrected as shown below:

Column 1, line 6: insert

--GOVERNMENT RIGHTS STATEMENT

This invention was funded, at least in part, with a government grant from the Department of Commerce, NIST-ATP Grant Number 70NANB8H4049. The United States Government may therefore have certain rights in this invention.--

Signed and Sealed this
Fifth Day of July, 2011

David J. Kappos
*Director of the United States Patent and Trademark Office*